US007835869B2

(12) United States Patent
Tsipouras et al.

(10) Patent No.: US 7,835,869 B2
(45) Date of Patent: Nov. 16, 2010

(54) METHOD AND APPARATUS FOR COMPUTER CONTROLLED RARE CELL, INCLUDING FETAL CELL, BASED DIAGNOSIS

(75) Inventors: Petros Tsipouras, Madison, CT (US); Triantafyllos Tafas, Rocky Hill, CT (US)

(73) Assignee: Ikonisys, Inc., New Haven, CT (US)

( * ) Notice: Subject to any disclaimer, the term of this patent is extended or adjusted under 35 U.S.C. 154(b) by 949 days.

(21) Appl. No.: 11/272,613

(22) Filed: Nov. 14, 2005

(65) Prior Publication Data
US 2006/0068376 A1 Mar. 30, 2006

Related U.S. Application Data

(60) Continuation of application No. 10/091,360, filed on Mar. 4, 2002, now Pat. No. 7,640,112, which is a continuation of application No. 09/724,384, filed on Nov. 28, 2000, now abandoned, which is a division of application No. 09/421,956, filed on Oct. 20, 1999, now abandoned, which is a continuation of application No. PCT/US99/10026, filed on May 7, 1999.

(60) Provisional application No. 60/084,893, filed on May 9, 1998.

(51) Int. Cl.
G06F 19/00 (2006.01)
G06K 9/00 (2006.01)
G06K 9/20 (2006.01)
G06K 9/78 (2006.01)

(52) U.S. Cl. .................. 702/19; 382/128; 382/133; 382/282; 382/286; 382/305

(58) Field of Classification Search .................. None
See application file for complete search history.

(56) References Cited

U.S. PATENT DOCUMENTS 3,586,064 A 6/1971 Brown et al.

(Continued)

FOREIGN PATENT DOCUMENTS

EP 0 595 506 5/1994

(Continued)

OTHER PUBLICATIONS

U.S. Appl. No. 09/421,956, filed Oct. 20, 1999.

(Continued)

Primary Examiner—Lori A Clow
(74) Attorney, Agent, or Firm—Kelley Drye & Warren LLP

(57) ABSTRACT

A computer controlled method for detecting and diagnosing a rare cell type in a tissue sample is provided, said method comprising treating the tissue sample such that it generates a first signal indicative of the presence at a location of a rare cell, detecting the first signal, treating the location at which the first signal is detected to generate a second signal indicative of a diagnostically useful cellular characteristic and detecting the second signal. The first signal can be morphological or a color present in a sought cell either before or after staining. The second signal can be generated by in situ PCR or PCR in situ hybridization. In one preferred embodiment, the rare cell type is a fetal cell in a maternal blood tissue sample, said sample consisting of a smear of unenriched maternal blood. In another embodiment, the method is used to diagnose or genotype cancer cells in a blood or tissue biopsy sample.

32 Claims, 10 Drawing Sheets

U.S. PATENT DOCUMENTS

| | | | |
|---|---|---|---|
| 3,887,466 A | | 6/1975 | Ayres |
| 4,513,438 A | | 4/1985 | Graham et al. |
| 4,641,927 A | | 2/1987 | Prescott et al. |
| 4,828,716 A | | 5/1989 | Mcewen et al. |
| 4,983,044 A | | 1/1991 | Schweber |
| 5,073,857 A | | 12/1991 | Peters et al. |
| 5,233,197 A | | 8/1993 | Bowman et al. |
| 5,287,272 A | * | 2/1994 | Rutenberg et al. .......... 382/224 |
| 5,352,613 A | | 10/1994 | Tafas et al. |
| 5,499,097 A | | 3/1996 | Ortyn et al. |
| 5,645,715 A | | 7/1997 | Coombs |
| 5,681,741 A | | 10/1997 | Atwood et al. |
| 5,740,269 A | | 4/1998 | Oh et al. |
| 5,764,792 A | | 6/1998 | Kennealy |
| 5,859,700 A | | 1/1999 | Yang |
| 5,889,881 A | | 3/1999 | MacAulay et al. |
| 5,936,731 A | | 8/1999 | Cabib et al. |
| 5,949,556 A | | 9/1999 | Tamai |
| 5,995,645 A | | 11/1999 | Soenksen et al. |
| 6,005,964 A | | 12/1999 | Reid et al. |
| 6,026,174 A | | 2/2000 | Palcic et al. |
| 6,049,421 A | | 4/2000 | Raz et al. |
| 6,087,134 A | | 7/2000 | Saunders |
| 6,136,540 A | | 10/2000 | Tsipouras et al. |
| 6,140,997 A | | 10/2000 | Tanaka |
| 6,151,405 A | | 11/2000 | Douglas et al. |
| 6,169,816 B1 | * | 1/2001 | Ravkin ...................... 382/128 |
| 6,211,955 B1 | | 4/2001 | Basiji et al. |
| 6,215,892 B1 | | 4/2001 | Douglas et al. |
| 7,133,543 B2 | | 11/2006 | Verwoerd et al. |
| 2002/0160443 A1 | | 10/2002 | Tsipouras et al. |
| 2004/0072364 A1 | | 4/2004 | Tisone et al. |

FOREIGN PATENT DOCUMENTS

| | | |
|---|---|---|
| EP | 0 713 086 B1 | 4/1999 |
| WO | WO 93/18186 | 9/1993 |
| WO | WO 94/02646 | 2/1994 |
| WO | WO 97/20198 | 6/1997 |
| WO | WO 97/43732 | 11/1997 |
| WO | WO 99/02960 | 1/1999 |
| WO | WO 99/08091 | 2/1999 |
| WO | WO 99/58972 | 11/1999 |

OTHER PUBLICATIONS

U.S. Appl. No. 09/724,384, filed Nov. 28, 2000.
U.S. Appl. No. 10/091,360, filed Mar. 4, 2002.
U.S. Appl. No. 11/833,154, filed Aug. 2, 2007.
U.S. Appl. No. 11/833,183, filed Aug. 2, 2007.
U.S. Appl. No. 11/833,203, filed Aug. 2, 2007.
U.S. Appl. No. 11/833,204, filed Aug. 2, 2007.
U.S. Appl. No. 11/833,428, filed Aug. 3, 2007.
U.S. Appl. No. 11/833,517, filed Aug. 3, 2007.
U.S. Appl. No. 11/833,594, filed Aug. 3, 2007.
U.S. Appl. No. 11/833,849, filed Aug. 3, 2007.
U.S. Appl. No. 12/013,944, filed Jan. 14, 2008.
U.S. Appl. No. 60/084,893, filed May 9, 1998.
Adnane, J. 1991 Oncogene 6:659-661.
Alitalo, K et al., 1986 Adv. Cancer Res. 47:235-281.
Dutrillaux, B. et al. 1990 Cancer Genet Cytogenct 49: 203-217.
Glasby et al. (Image Analysis for Biological Sciences (1995) John Wiley and Sons, Chichester, England, pp. 31-38).
International Search Report, International Application No. PCT/US99/10026, International Filing Date, May 7, 1999.
Kalliomiemi, A. et al 1994 Proc. Natl. Acad. Sci. USA 91:2156-2160.
Kalliomiemi, A. et al. 1992 Science 258:818-821.
Mergenthaler et al. 2005 J. Histochem. Cytochem., 53(3): 319-322.
Press, M. F. et al. 2002 J. Clin. Oncol. 20 (14):3095-3105.
Ross, J. S. et al. 2003 The Oncologist vol. 8, No. 4, 307-325.
Schwab, M. 1990 Genes Chromosomes Cancer 1:181-193.
Slamon, D. J. et al. 1987 Science 235:178-182.
So, C_K et al. 2004 Clinical Cancer Research 10: 19-27.
Zafrani, B. et al. 1992 Human Pathology 23: 542-547.
Glasbey et al. (Image Analysis for Biological Sciences(1995) John Wiley and Sons, Chichester, England, pp. 31-38).
Baxes, 1994, "Digital Image Processing, Passage," U.S., New York, Wiley, pp. 127-137.
Lizardi et al., 1998, "Mutation Detection and Single-Molecule Counting Using Isothermal Rooling-Circle Amplification," Nature Genetics, 19(3): pp. 225-232.
Mesker et al., 1994, "Detection of ImmunocytochemicallyStained Rare Events Using Image Analysis," Cytochemistry 17: pp. 209-215.
Oosterwijk et al., 1998, "Strategies for Rare-Event Detection: An Approach for Automated Fetal Cell Detection in Maternal Blood," Am. J. Hum. Genet. 63: pp. 1783-1792.
Oosterwijk et al., 1998, "Development of a Preparation and Staining Method for Fetal Erythroblasts in Maternal Blood: Simultaneous Immunocytochemical Staining and FISH Analysis," Cytometry 32: pp. 170-177.
Oosterwijk et al., 1998, "Fetal Cell Detection in Maternal Blood: A study in 236 Samples Using Erythroblast Morphology, DAB and HbF Staining, and FISH Analysis," Cytometry 32: pp. 178-185.
Tanke et al., 1996, "Detection of "Rare Event" Fetal Erythroblasts in Maternal Blood Using Automated Microscopy," Early Hum. Devel. 47 Suppl.: pp. S89-S93.
Verwoerd et al., 1987, "Somatic Cell Mutations In Humans Detected by Image Analysis of Immunofluorescently Stained Erythrocytes," in: *Clinical Cytometry and Histometry*, Burger et al., eds., Academic Press, pp. 465-469.
"XL VISION Announces Advanced Imaging Technology for Early Detection of Metastatic Cancer," Press Release dated Dec. 18, 1995, XL Vision, Sebastian, FL, pp. 7-11.
International Search Report, International Application No. PCT/US02/31684, International Filing Date, Dec. 23, 2002.
AneuVysion® Multicolor DNA Probe Kit by Vysis division of Abbott Laboratories http://www,aneuvysion.com/AboutAneuVysion_ 6.asp pp. 1-3, Mar. 31, 2006.
UroVysion® kit by Vysis division of Abbott Laboratories http://www.urovysion.com/UroVysionBladderCancerKit_353.aspx p. 1, Mar. 21, 2007.

* cited by examiner

METHOD AND APPARATUS FOR COMPUTER CONTROLLED RARE CELL, INCLUDING FETAL CELL, BASED DIAGNOSIS

RELATED APPLICATIONS

This application is a continuation of U.S. patent Ser. No. 10/091,360, filed on Mar. 4, 2002, now U.S. Pat. No. 7,640,112, which is a continuation of U.S. patent application Ser. No. 09/724,384, filed Nov. 28, 2000, now abandoned, which is a divisional of U.S. patent application Ser. No. 09/421,956, filed Oct. 20, 1999, now abandoned, which is a continuation of PCT/US99/10026, filed May 7, 1999, which claims priority of U.S. Provisional Patent Application No. 60/084,893, filed May 9, 1998, all disclosures of which are incorporated by reference herein in their entirety.

1. FIELD OF THE INVENTION

The present invention relates to computer controlled methods and apparatus for obtaining and preparing cell samples and for identifying a rare cell of interest from a field of cells and making a diagnosis based on a characteristic of a rare cell selected in the field. In one important embodiment, the invention relates to obtaining and preparing a maternal blood sample for fetal cell based prenatal diagnosis.

2. BACKGROUND OF THE INVENTION

The advent of DNA based prenatal diagnosis for human genetic disorders has led to the development of a number of new diagnostic methods. These diagnostic methods permit early detection and consequently informed decisions and intervention with respect to fetus having a genetic disorder. These methods, however, have a number of disadvantages. Each of the new diagnostic methods with which this discussion is concerned requires that a sample of isolated fetal cells be obtained, so that the DNA of the fetus may be examined or tested for signs of specific genetic disorders. The disadvantages of these modern methods stem primarily from the need to obtain a sample of fetal cells. Currently, fetal cells are obtained by invasive procedures requiring obstetric intervention by amniocentesis or by chorionic villus sampling. These highly specialized procedures carry a small, but significant, risk to the fetus. Early in pregnancy, the level of risk to the fetus is high and the number of cells obtained is low. Therefore, results of these procedures often are not obtained until 18-20 weeks of pregnancy.

One modern procedure for obtaining fetal cells relies on leakage of fetal cells into the maternal circulation. By simply drawing a sample of maternal blood, it is theoretically possible to obtain fetal cell material in a sufficient quantity for prenatal diagnosis by DNA based methods. Obtaining fetal cells from the maternal blood circulation avoids any risk to the fetus and can be undertaken as early as 10-12 weeks of pregnancy.

Fetal cells which have been detected in the maternal blood circulation include trophoblasts, lymphocytes and nucleated erythrocytes. Trophoblasts were the first fetal cells to be identified in the maternal blood circulation, due to their large size. However, nucleated erythrocytes have generated the greatest degree of interest as sources of genetic material for prenatal diagnosis due to their rarity in the adult blood circulation, their abundance in fetal blood and their limited life span. These factors combine to reduce errors in distinguishing fetal cell material from maternal cell material. Fetal cells circulating in the maternal blood have a life span ranging from a few weeks (for the nucleated erythrocytes) to a few years (for the lymphocytes).

Although they are consistently present in the maternal blood circulation, fetal cells are very rare, severely limiting their diagnostic utility. Estimates of the concentration of fetal cells within the maternal blood circulation vary widely, from a high level of 1 fetal cell in $10^5$ maternal cells, to a low level of one fetal cell in $10^9$ maternal cells. Thus, a 10 ml sample of maternal blood will ordinarily contain between about 10 and 100 fetal cells. Throughout this description, the concentration of fetal cells found in a freshly drawn maternal blood sample, prior to any further treatment, is referred to as the "naturally present concentration" of fetal cells, typically, but not necessarily, within the above ranges. Also throughout this description, the term "unenriched maternal blood" shall refer to a sample of maternal blood which contains only a naturally present concentration of fetal cells.

Since the naturally present concentration of fetal cells in unenriched maternal blood is so low, in order to obtain a diagnostically significant sample of fetal cells modern techniques include methods of physically isolating the fetal cells from the maternal cells in the sample. In essence, modern techniques are methods of concentrating the fetal cells within a sample, i.e., enriching the sample, for example by removing excess maternal cells, without removing fetal cells. These methods are extremely difficult to perform, often fail to isolate a sufficient number of fetal cells to be diagnostically significant and sometimes fail to provide a sample of a sufficient number of undamaged fetal cells of adequate purity for reliable subsequent diagnosis.

3. SUMMARY OF THE INVENTION

It is desired to provide a computer controlled method and apparatus for detecting and diagnosing a rare cell type in a tissue sample, said diagnosis being based upon a characteristic of that rare cell. It is further desired to provide a computer controlled method and apparatus for detecting fetal cells in a blood preparation and performing a fetal cell based prenatal diagnosis that solves the above-identified problems, which overcomes such other problems and meets such other goals as will be apparent to the person skilled in this art after reading a description of the invention.

Generally, the invention provides a computer-implemented method of processing body fluid or tissue sample image data, the method comprising creating a subset of a first image data set representing an image of a body fluid or tissue sample taken at a first magnification, the subset representing a candidate blob which may contain a rare cell creating a subset of a second image data set representing an image of the candidate blob taken at a second magnification, the subset of the second data set representing the rare cell and storing the subset of the second data set in a computer memory.

In general, a subset of a first image data set can be created by observing an optical field of a monolayer of cells from a body fluid or tissue sample using a computerized microscopic vision system to detect a signal indicative of the presence of a rare cell.

The method further comprises contacting a body fluid or tissue sample at a location corresponding to each candidate blob represented in the subset of the first image data set, with a reagent to generate a medically significant signal. This method provides the advantage of being able to remove from further processing a body fluid or tissue sample for which no subset of the first data set representing a candidate blob is created. The signal can be measured to determine whether it is a significant signal level. The first and/or the second image data subsets can be transformed into a representation that is more suitable for control and processing by a computer as described herein. In a preferred embodiment, the image data is transformed from an RGB (Red Green Blue) signal into an HLS (Hue Luminescence Saturation) signal. Filters and/or masks are utilized to distinguish those cells that meet pre-selected criteria and eliminate those that do not, and thus identify rare cells.

In another aspect of the invention, there is provided a method of operating a laboratory service, the method comprising steps of receiving a body fluid or tissue sample, creating a body fluid or tissue sample smear, operating a computerized microscope so that a software program automatically identifies a rare cell in the smear and detecting a medically significant signal in the rare cell.

In yet another aspect of the invention, there is provided computer software product including a computer-readable storage medium having fixed therein a sequence of instructions which when executed by a computer direct performance of steps of detecting and diagnosing a rare cell type. The cells encompass: creating a subset of a first image data set representing an image of a body fluid or tissue sample taken at a first magnification, the subset representing a candidate blob which may contain a rare cell creating a subset of a second image data set representing an image of the candidate blob taken at a second magnification, the subset of the second data set representing the rare cell and storing the subset of the second data set in a computer memory.

In general, a subset of a first image data set can be created as described above. The steps further encompass contacting a body fluid or tissue sample at a location corresponding to each candidate blob represented in the subset of the first image data set, with a reagent to generate a medically significant signal. This provides the advantage of being able to remove from further processing a body fluid or tissue sample for which no subset of the first data set representing a candidate blob is created. There is an optional step by which the signal can be measured to determine whether it is of a significant level. Another optional step encompasses transformation of one or both of the first and the second image data subsets into a representation that is more suitable for control and processing by a computer as described herein. In a preferred embodiment, the image data is transformed from an RGB (Red Green Blue) signal into an HLS (Hue Luminescence Saturation) signal. Filters and/or masks are utilized to distinguish those cells that meet pre-selected criteria and eliminate those that do not.

According to one aspect of the invention, there is provided a method of preparing a sample of cells for a diagnostic procedure. The sample of cells is obtained and fixed as a monolayer on a substrate, the sample of cells including a rare cell which is present in the sample at no greater than one in every 10,000 cells (i.e. no greater than 0.01%).kl An optical field covering at least a portion of the sample of cells is observed using a computerized microscopic vision system for a signal indicative of the presence of a rare cell. The signal is detected, and coordinates where the signal is detected are identified, for the diagnostic procedure. In one embodiment the rare cell is present at no greater than 0.001% of the cells. In other embodiments the rare cell is present at no greater than 0.0001%, 0.00001% or even 0.000001%.

In one particularly important embodiment, the rare cell is a fetal cell in a sample of cells from maternal blood. In a preferred embodiment, the sample contains only a naturally present concentration of fetal cells which can be no greater than 0.001%, 0.0001%, 0.00001%, 0.000001% or even 0.0000001%.

In another specific embodiment of the invention, the rare cell type to be detected and diagnosed is a cancer cell found in a sample of cells or tissue from an animal or patient. The sample can be blood or other body fluid containing cells or a tissue biopsy. As an illustration of this embodiment, cancer cell markers described in Section 5, infra, e.g. GM4 protein, telomerase protein or nucleic acids, and p53 proteins or nucleic acids, may be used in the generation of the first or second signal, in a manner to be determined by the specific application of the invention.

In one embodiment of the invention, when the rare cell type is present in the sample, the method of the invention detects the rare cell type at a frequency of no less than 80%. In other embodiments, the detection frequencies are no less than 85%, 90%, 95% and 99%.

According to one particularly important embodiment of the invention, there is provided a method of preparing a sample of blood for a diagnostic procedure, which includes: preparing a smear of a sample of unenriched maternal blood containing a naturally present concentration of fetal cells; observing an optical field covering a portion of the smear using a computerized microscopic vision system for a signal indicative of the presence of a fetal cell; detecting said signal; and identifying, for the diagnostic procedure, coordinates within the smear at which the signal is detected.

In one embodiment, the signal is further processed to represent morphological measurements of the rare cell. In another embodiment, the cells are treated with a label to enhance the optical distinction of rare cells from other cells. In this embodiment, the signal can be, for example, from a label which selectively binds to the rare cells. In another embodiment, the diagnostic procedure involves moving to the coordinates identified and magnifying the optical field until the image is of an isolated rare cell.

In some embodiments, the optical field is stepped over a sequence of portions of the cells covering substantially all of the cells. This may be achieved, for example, by moving the cells on the substrate under control of the computerized microscopic vision system relative to a lens of the computerized microscopic vision system. In another embodiment, the coordinates at which the first signal was obtained are identified, and then the rare cell at those coordinates specifically is contacted after the coordinates have been identified.

According to another aspect of the invention, there is provided a method of obtaining from a sample of cells a signal having diagnostic significance relative to a rare cell in the sample of cells. The rare cell is present in the sample at no greater than one in every 10,000 cells. The method includes preparing a monolayer of the sample of cells fixed on a substrate. The rare cell is contacted with an agent to generate a diagnostic signal, the diagnostic signal having the diagnostic significance. The monolayer is observed using a computerized microscopic vision system to obtain the diagnostic signal. In some embodiments, the diagnostic signal can be used to identify the rare cell. In other embodiments, a locating signal can be used to identify the rare cell, and the diagnostic signal is obtained after the cell is located.

In one embodiment, the rare cell is present in the sample at no greater than one in every 10,000 cells (i.e. no greater than 0.01% of the cells). In other embodiments, the rare cell is present at no greater than 0.001%, 0.00001% or even 0.000001%. In one particularly important embodiment, the rare cell is a fetal cell in a sample of cells from maternal blood. Preferably the sample contains only a naturally present concentration of fetal cells which can be no greater than 0.001%, 0.0001%, 0.00001%, 0.000001% or even 0.0000001%.

According to an important embodiment of the invention, there is provided a method of obtaining from a sample of unenriched maternal blood, containing a naturally present concentration of fetal cells, a signal having diagnostic significance relative to the fetal cells. The method includes: preparing a smear of the sample of unenriched maternal blood; observing the smear using a computerized microscopic vision system to obtain a first signal indicative of the presence of a fetal cell; contacting the fetal cell with an agent to generate a second signal, the second signal having the diagnostic significance; and observing the fetal cell using the computerized microscopic vision system to obtain the second signal. In one embodiment, the smear can comprise at least 250 µl of the unenriched maternal blood and even can comprise at least 500 µl of the unenriched blood.

As described above, the first signal can be further processed to represent morphological measurements of the rare cell. Likewise, the cells can be treated with a label to enhance optical distinctions of rare cells from other cells, such as maternal cells. To achieve this, the first signal can be from a label which selectively binds to the rare cell, such as a fetal cell. Likewise, as above, the step of observing can involve stepping an optical field over a sequence of portions of the cells, which can be accomplished, for example, by moving the cells or the substrate under control of the computerized microscopic vision system relative to a lens of the computerized microscopic vision system. In any of the foregoing embodiments, the cells can be prepared on a substrate, and a coordinate system can be calibrated to the substrate so that coordinates of the rare cell identified in one step can be returned to later in another step. Likewise, the substrate in certain important embodiments has a length that is 10 times its width, the substrate being substantially elongated in one direction. The length can even be 20 times the width. The substrate can be a flexible film, and in one important embodiment, is an elongated flexible film that can carry a relatively large volume of cells, such as would be provided from a relatively large volume of smeared maternal blood.

In any of the foregoing embodiments, the first signal and the second signal can be selected whereby they do not mask one another when both are present. Likewise, in any of the foregoing embodiments, the second signal can be generated by in situ PCR or PCR in situ or fluorescence in situ hybridization (FISH).

In one important embodiment, the substrate is a plurality of substrates on which the sample of cells is prepared, such as a plurality of smears of maternal blood, each of the plurality including a total of at least 5 µl of the sample. A rare cell-containing substrate (in which the first signal is obtained) is identified. Then, only the rare cell-containing substrate/substrates which has/have been identified is/are treated to generate the second signal.

According to yet another aspect of the invention, there is provided a method of performing a diagnosis for a fetus, using an unenriched sample of maternal blood containing naturally present fetal cells. This method includes: preparing a smear of at least 250 µl of the sample of unenriched maternal blood; identifying a fetal cell within the smear; contacting the fetal cell with an agent that produces a diagnostic signal; and observing the diagnostic signal. In one important embodiment, the step of identifying can comprise observing cells within the smear, using a computerized microscopic vision system, measuring a signal produced by the observed cells indicative of the presence of fetal cells, and defining coordinates at which the measured signal indicates the presence of the fetal cell. Important embodiments directed to volumes of the maternal blood, substrate configurations and so forth are as described above.

According to yet another aspect of the invention, there is provided a method of obtaining from a sample of unenriched maternal blood containing a naturally present concentration of fetal cells, an image of a substantially isolated fetal cell. This method includes: preparing a smear of at least 250 µl of the sample of unenriched maternal blood; observing the smear with a computerized microscopic vision system for a signal indicative of the presence of a fetal cell; identifying coordinates at which the signal is observed; moving to the coordinates identified, an optical field including an image of the fetal cell; and magnifying the optical field until the image is of an isolated fetal cell. Important embodiments directed to volumes of the maternal blood sample, substrate configurations and so forth are as described above.

According to yet another aspect of the invention, there is provided a device for screening fetal cells contained within a smear of an unenriched sample of maternal blood containing a naturally present concentration of fetal cells, comprising: a flexible film having thereon a smear of at least 250 µl of maternal blood. In one embodiment, the flexible film has thereon a smear of at least 500 µl of maternal blood. In one important embodiment, the flexible film is an elongated film, the length being at least 10 times the width. It is particularly preferred that the flexible film include marking coordinates, whereby the computerized microscopic vision system described herein can locate a cell relative to a point on the film, permitting that cell to be returned to at a later time, if desired.

According to yet another aspect of the invention, there is provided a device for screening rare cells contained within a sample of cells at a concentration of no greater than one rare cell for every 10,000 cells in the sample of cells. The device is a flexible film having fixed thereon the sample of cells, wherein the flexible film is at least five inches long. In one preferred embodiment the flexible film has a length at least 10 times its width. In another important embodiment, the flexible film includes marking coordinates, whereby the computerized microscopic vision system described herein can locate a cell relative to a point on the film, permitting the cell to be returned to at a later time, if desired.

According to another aspect of the invention, there is provided a device for dispensing materials to a specific location on a slide. The device includes a microscopic vision system for detecting a signal indicative of the presence of a rare cell in a sample of cells. The device also includes means for identifying the coordinates of the rare cell in an optical field. The device further has attached to it a dispenser for dispensing a volume of material and means for moving the dispenser to the coordinates whereby the volume of material may be dispensed upon the rare cell. The material dispensed can be reagents such as a label, PCR, primers, and the like.

According to another important embodiment of the invention, the need for scanning large areas of microscopic preparations in the minimum possible amount of time is met by the use of an apparatus or system that provides a "composed" image. It is based on the simultaneous use of an array of computer controlled objective lenses, arranged on a support system and having the capacity to focus on a microscopic preparation. Each of the objective lenses is connected to a charge coupled device camera, herein referred to as a CCD camera, being connected to image acquisition hardware installed in a host computer. The images are stored in the computer memory and they are combined in an appropriate side to side fashion, so that a "composed" image is formed in the computer memory. The "composed" image can be further processed as a unity, using any kind of imaging procedures to detect specific features that are in question. The significant advantage of the described system consists in its capacity to acquire images simultaneously from a number of objective lenses, thus minimizing the time needed to process large areas of the sample in a manner that is inversely proportional to the number of objectives used.

The "composing" system can process any kind of microscopic preparation using either transmitted or reflected light. It is particularly useful where large numbers of samples need to be processed imposing significant time constraints, for example, for processing large numbers of microscopic biological preparations for screening and/or diagnostic purposes, etc.

4. BRIEF DESCRIPTION OF THE DRAWINGS

In the accompanying drawings, in which like reference designations indicate like elements:

Figure 4A:
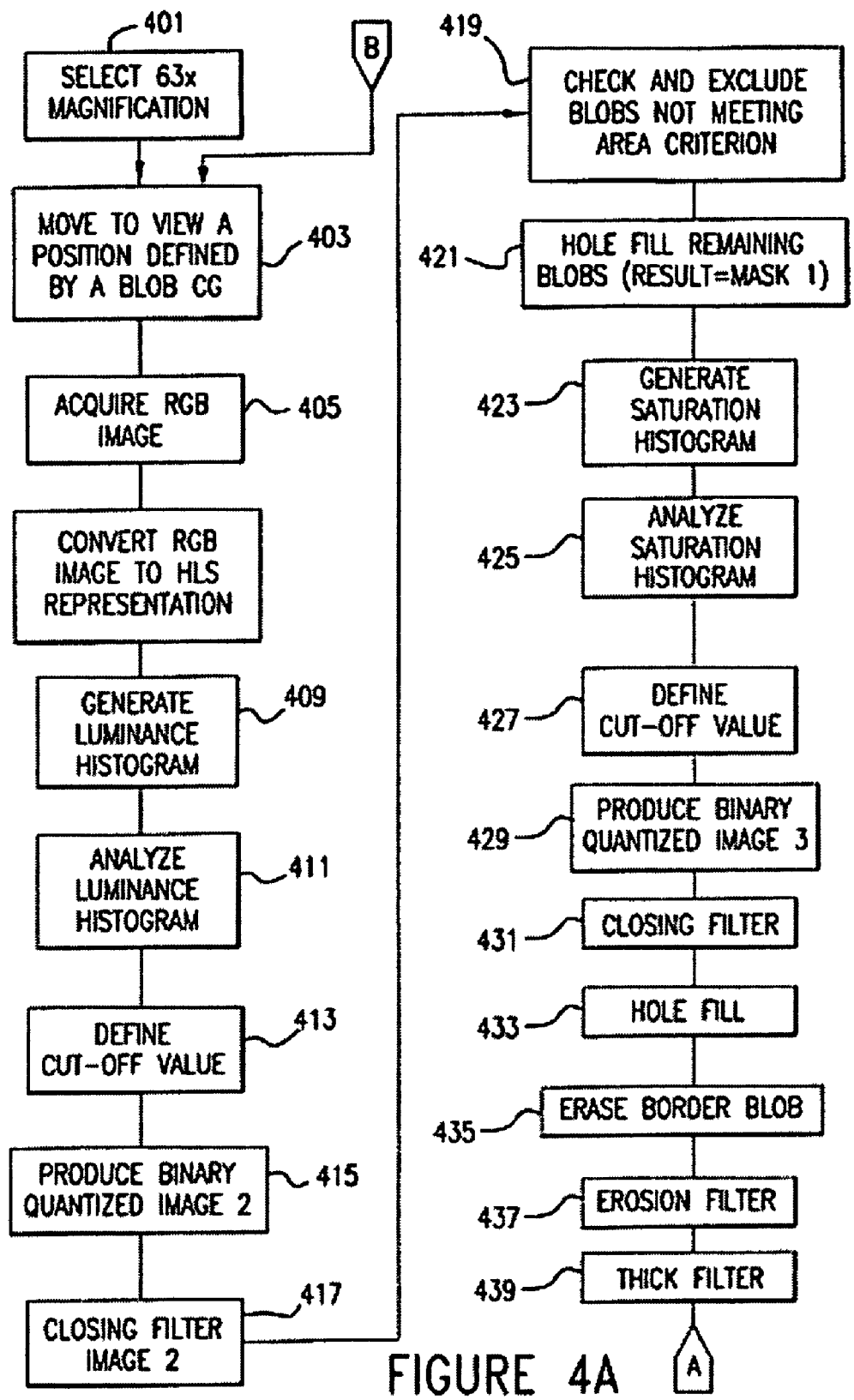
Figure 4B:
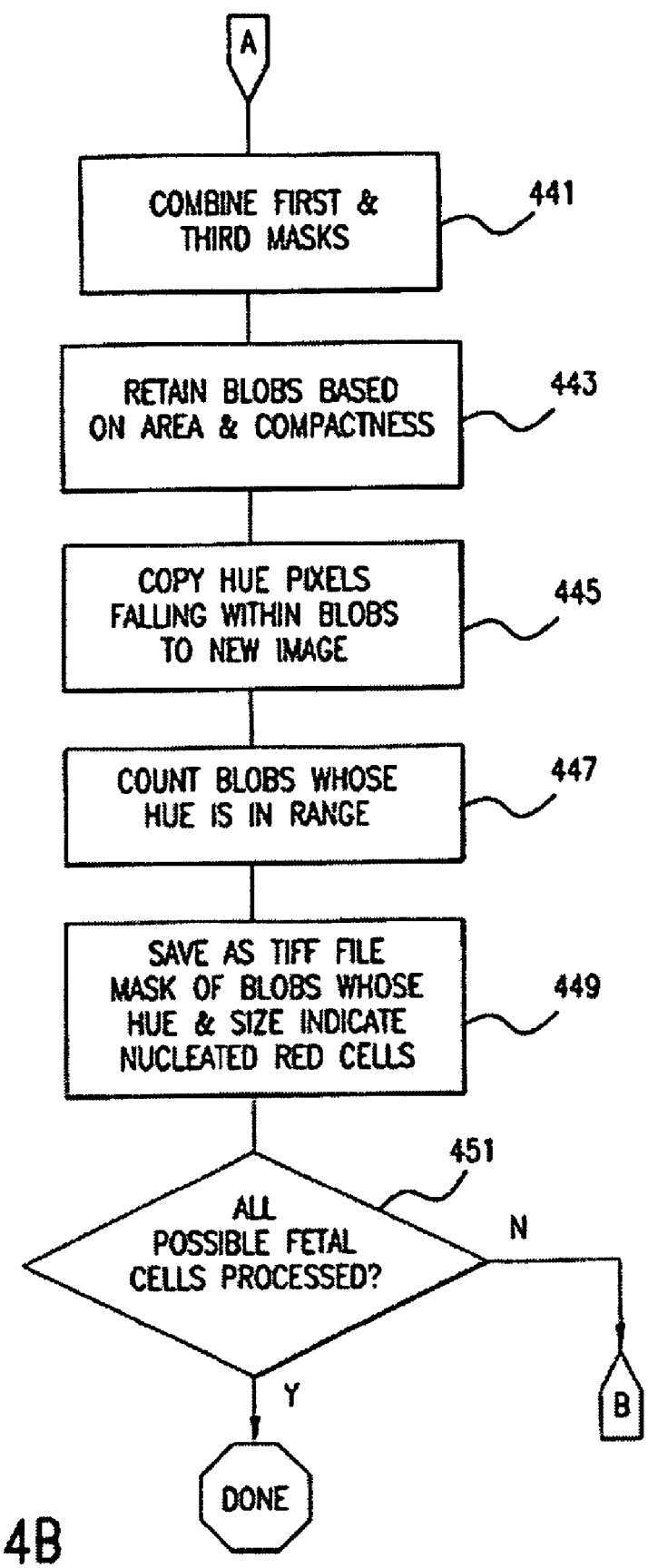
Figure 5:
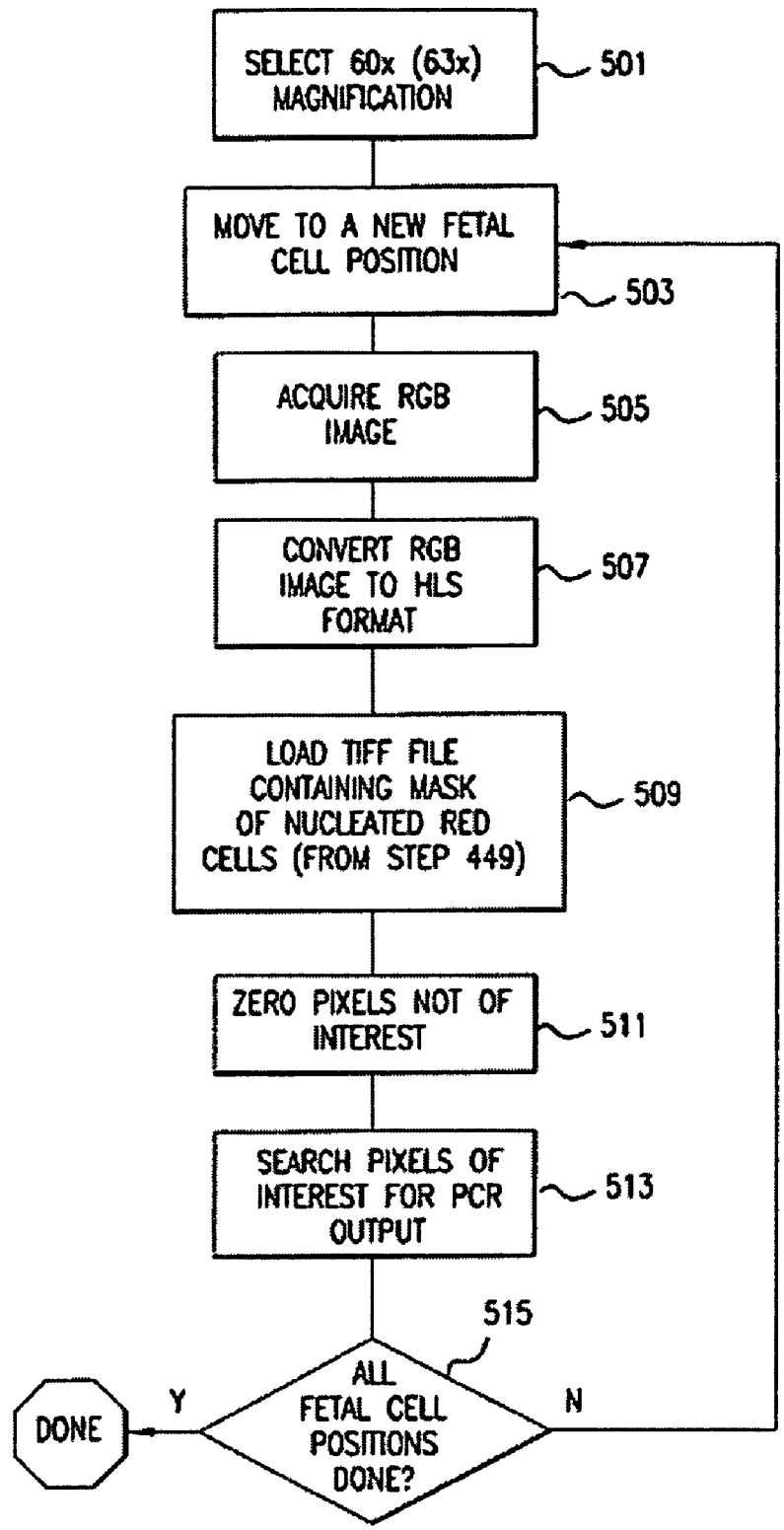
Figure 6:
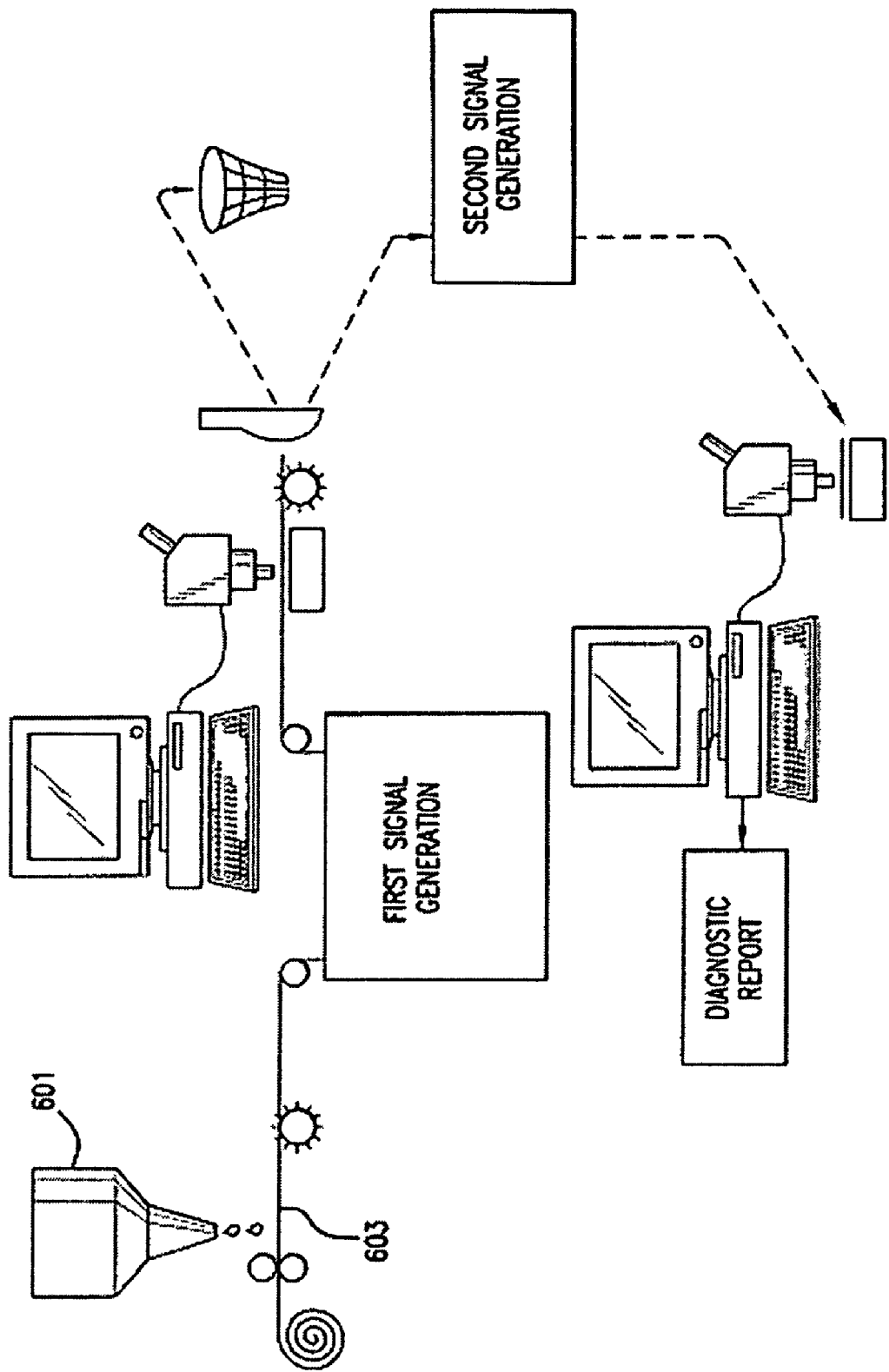
Figure 7:
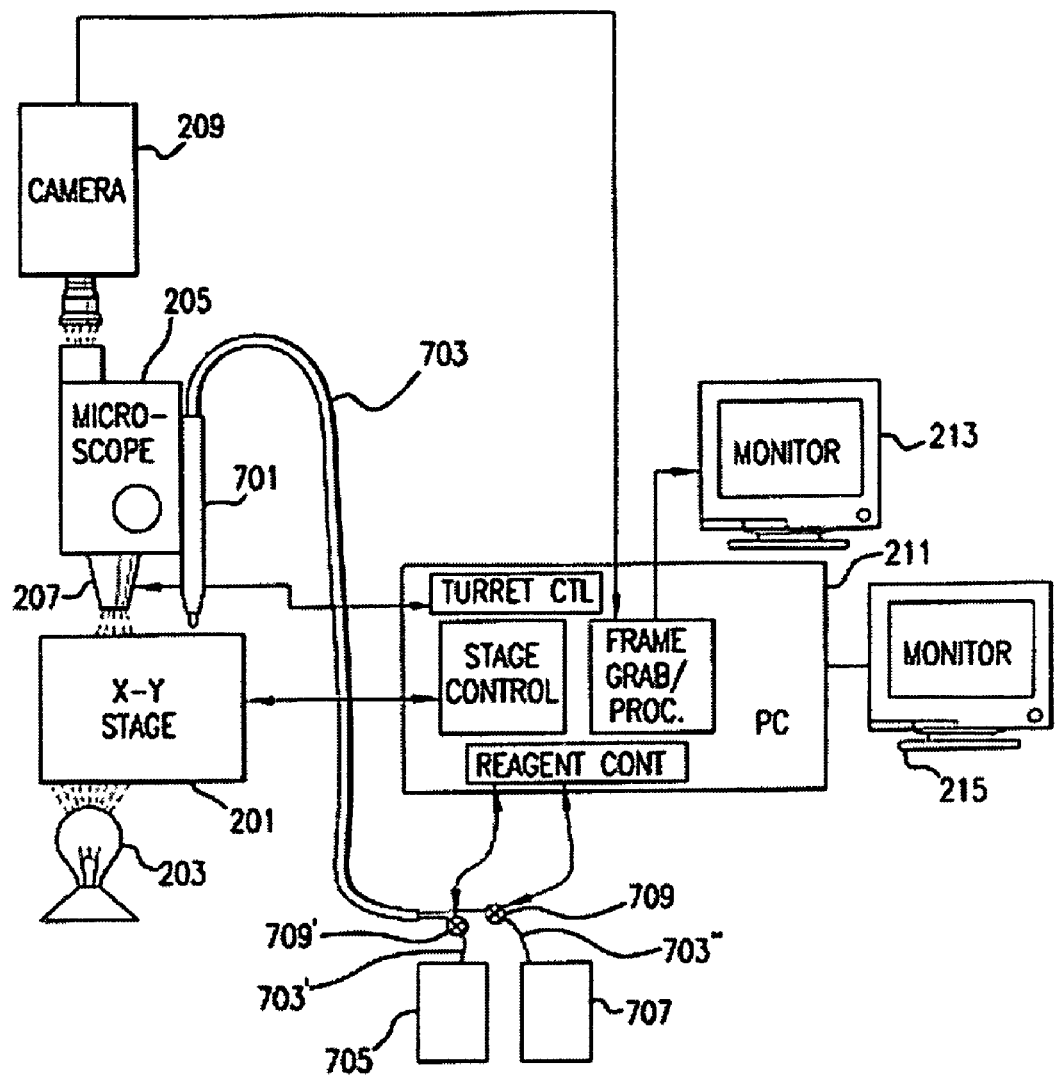
Figure 8:
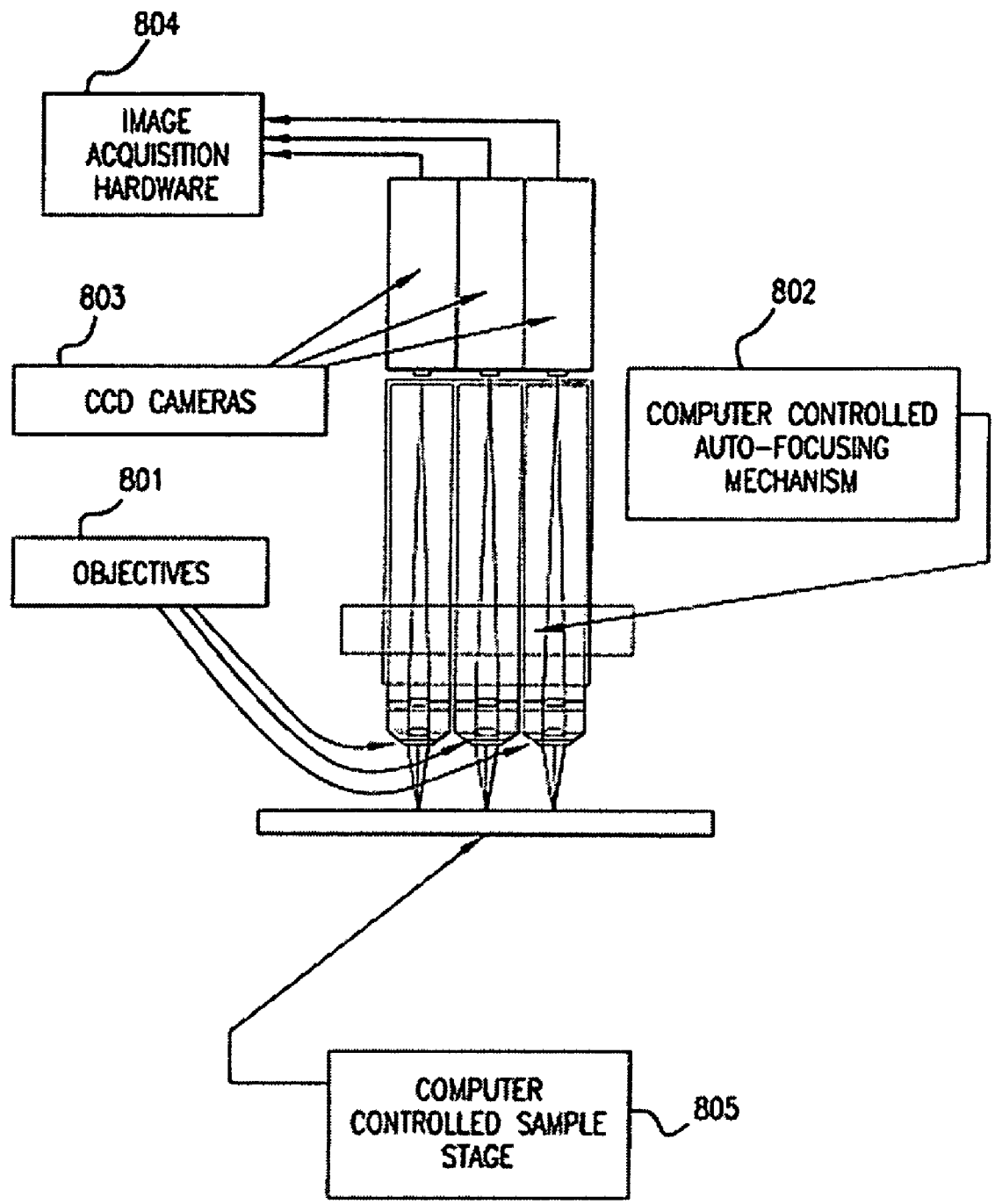

FIGS. 4A and 4B taken together are a flow chart of stage II leading to detecting the first signal;

FIG. 5 is a flow chart of detection of the second signal;

FIG. 6 is a schematic representation of a variation of an apparatus embodying aspects of the invention, using a continuous smear technique;

FIG. 7 is a block diagram of an analysis and reagent dispensing system used in one embodiment of one aspect of the invention;

FIG. 8 is an outline of a multiple objective microscopy system; and

Figure 9:
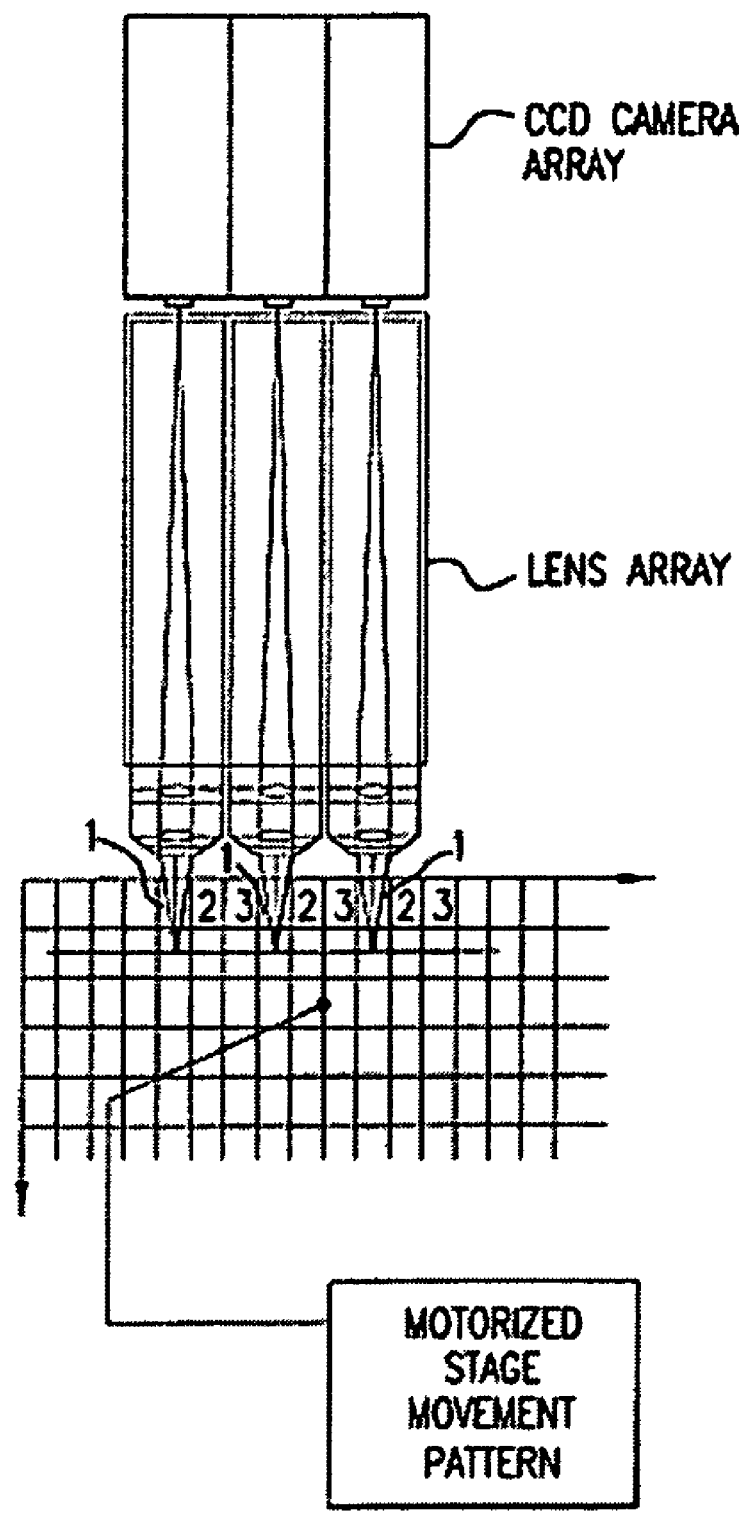

FIG. 9 is an image "composition" method.

5. DETAILED DESCRIPTION OF THE INVENTION

The invention will be better understood upon reading the following detailed description of the invention and of various exemplary embodiments of the invention, in connection with the accompanying drawings. While the detailed description explains the invention with respect to fetal cells as the rare cell type and blood as the body fluid or tissue sample, it will be clear to those skilled in the art that the invention can be applied to and, in fact, encompasses diagnosis based on any rare cell type and any body fluid or tissue sample for which it is possible to create a monolayer of cells on a substrate.

Body fluids and tissue samples that fall within the scope of the invention include but are not limited to blood, tissue biopsies, spinal fluid, meningeal fluid, urine, alveolar fluid, etc. For those tissue samples in which the cells do not naturally exist in a monolayer, the cells can be dissociated by standard techniques known to those skilled in the art. These techniques include but are not limited to trypsin, collagenase or dispase treatment of the tissue.

In an important specific embodiment, the invention is used to detect and diagnose fetal cells. Our approach is directly opposite to that taken by others seeking a non-invasive method for performing fetal cell based prenatal diagnosis. Rather than attempting substantially to enrich the concentration of fetal cells within a maternal blood sample, our approach involves identifying fetal cells within an unenriched maternal blood sample and subsequently performing diagnostic procedures on the fetal cells so identified, in situ.

Figure 1:
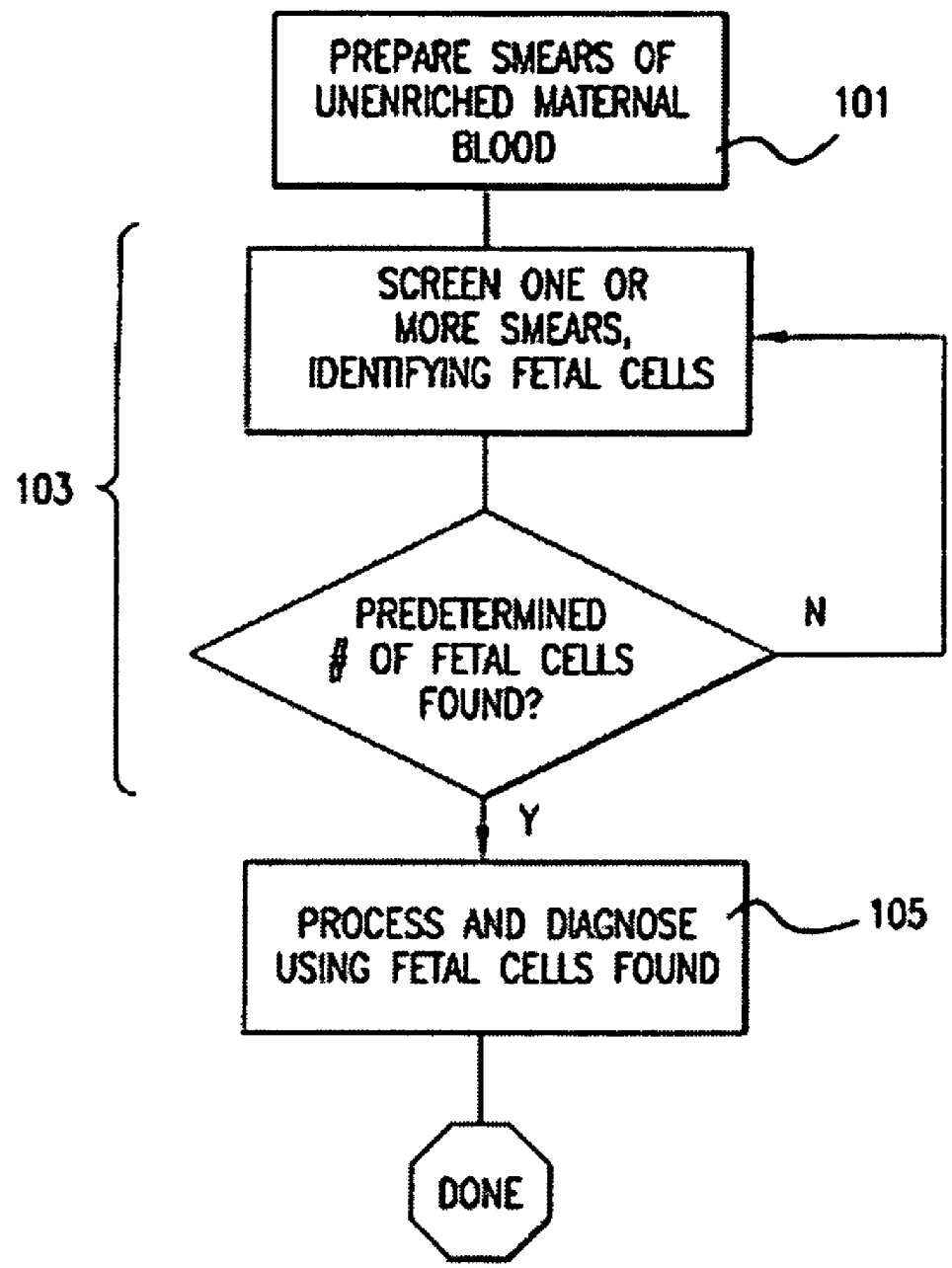
FIG. 1 is a flow chart summarizing the method of one aspect of the invention.

A summary of this new approach, shown in the flow chart of FIG. 1, is as follows:

Prepare one or more blood smears from a sample of unenriched maternal blood 101;

Screen the one or more blood smears until a predetermined number of fetal cells (e.g., nucleated erythrocytes) have been identified and their coordinates defined 103; and Process those smears or coordinates of a smear at which fetal cells have been identified, diagnosing the presence or absence of a particular genetic feature in the fetal cells 105.

In this approach, two signals are defined, referred to hereinafter as the first signal and the second signal. As used herein, "signal" should be taken in its broadest sense, as a physical manifestation which can be detected and identified, thus carrying information. One simple and useful signal is the light emitted by a fluorescent dye selectively bound to a structure of interest. That signal indicates the presence of the structure, which might be difficult to detect absent the fluorescent dye.

Screening 103 is based on the first signal. The first signal, which in this exemplary embodiment indicates cell identity, may be generated by a fluorescent dye bound to an antibody against the hemoglobin .epsilon.-chain, i.e., embryonal hemoglobin, for example.

Alternatively, for example, a metric of each cell's similarity to the characteristic morphology of nucleated erythrocytes, discerned using cell recognition algorithms may serve as the first signal. In yet another example, the first signal may be a measure of the presence of the characteristic color of fetal hemoglobin after staining with eosin and acid hematoxylin. It should now be evident that any detectable indicator of the presence of fetal cells may serve as the first signal, subject to certain constraints noted below.

Diagnosing 105 is based on the second signal. The second signal, which in this exemplary embodiment indicates the presence of a particular genetic characteristic being tested for, may be generated, for example, by in situ PCR-amplification or PCR in situ hybridization or FISH. Cells that emit both signals, i.e., the cell is a fetal cell and contains the genetic characteristic being tested for, will be scored. Counts may be maintained of the number and strengths of the first and second signals detected.

In one embodiment, a specific nucleic acid sequence is detected by FISH. In an exemplary embodiment, FISH comprises hybridizing the denatured test DNA of the rare cell type, e.g. a fetal cell, with a denatured dioxygenin (DIG)-labeled genomic probe. The samples containing the test DNA are washed and allowed to bind to an anti-DIG antibody coupled to a fluorophore. Optionally, a second layer of fluorophore (e.g. FITC) is added by incubation with fluorophore-conjugated anti-Fab antibodies. In a preferred embodiment, FISH comprises hybridizing the denatured DNA of the rare cell with a fluorescently labeled probe comprising DNA sequence(s) homologous to a specific target DNA region(s) directly labeled with a particular fluorophore.

Automated sample analysis will be performed by an apparatus and method of distinguishing in an optical field objects of interest from other objects and background. An example of an automated system is disclosed in our U.S. Pat. No. 5,352,613, issued Oct. 4, 1994. Furthermore, once an object has been identified, the color, i.e., the combination of the red, green, blue components for the pixels that comprise the object, or other parameters of interest relative to that object can be measured and stored.

Figure 3:
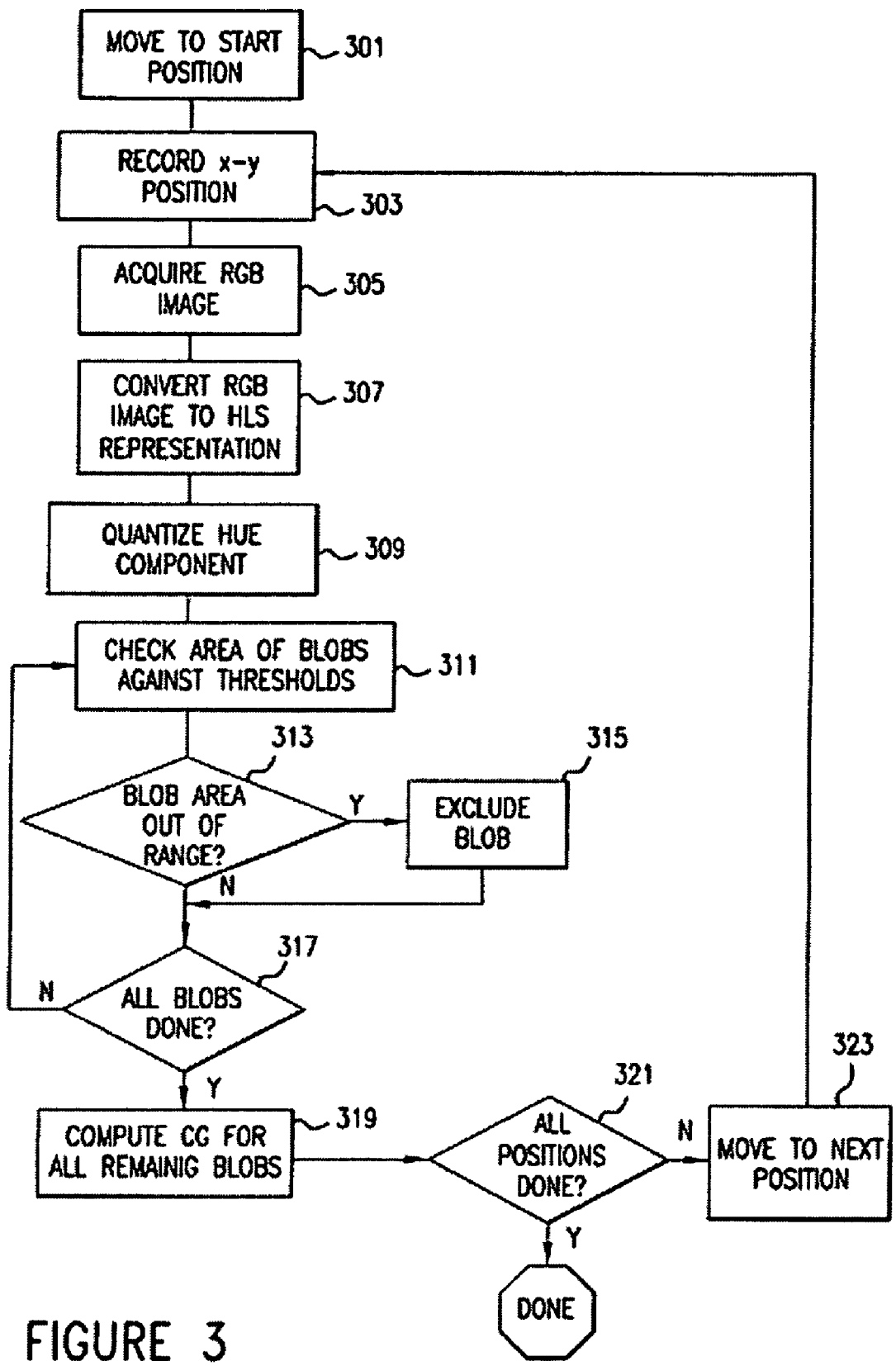
FIG. 3 is a flow chart of stage I leading to detecting the first signal.

Another example of an apparatus and method for automated sample analysis is presented, infra, in Section 6, Exemplary Embodiments, in particular Sections 6.2.1, 6.2.2 and 6.3, and is illustrated in FIGS. 3-5.

In one embodiment of the invention, the system consists of an automatic microscopical sample inspection system having:

a sample storage and loading and unloading module a sample transporting mechanism to and from an automated stage that moves the sample under a microscope objective lenses array an array of CCD cameras a processing unit having a host computer, multiple controllers to control all mechanical parts of the microscopy system and a high speed image processing unit where the CCD cameras are connected.

An innovative feature of this embodiment of a computer controlled system is an array of two or more objective lenses having the same optical characteristics, depicted in FIG. 8. The lenses are arranged in a row and each of them has its own z-axis movement mechanism, so that they can be individually focused (801). This system can be equipped with a suitable mechanism so that the multiple objective holder can be exchanged to suit the same variety of magnification needs that a common single-lens microscope can cover. Usually the magnification range of light microscope objectives extends from 1× to 100×.

Each objective is connected to its own CCD camera (803). The camera field of view characteristics are such that it acquires the full area of the optical field as provided by the lens.

Each camera is connected to an image acquisition device (804). This is installed in a host computer. For each optical field acquired, the computer is recording its physical location on the microscopical sample. This is achieved through the use of a computer controlled x-y mechanical stage (805). The image provided by the camera is digitized and stored in the host computer memory. With the current system, each objective lens can simultaneously provide an image to the computer, each of which comprises a certain portion of the sample area. The lenses should be appropriately corrected for chromatic aberrations so that the image has stable qualitative characteristics all along its area.

The imaged areas will be in varying physical distance from each other. This distance is a function of the distance at which the lenses are arranged and depends on the physical dimensions of the lenses. It will also depend on the lenses' characteristics, namely numerical aperture and magnification specifications, which affect the area of the optical field that can be acquired. Therefore, for lenses of varying magnification/numerical aperture, the physical location of the acquired image will also vary.

The computer will keep track of the features of the objectives-array in use as well as the position of the motorized stage. The stored characteristics of each image can be used in fitting the image in its correct position in a virtual patchwork, i.e. "composed" image, in the computer memory as shown in FIG. 9.

For example, when starting the host computer moves the sample stage to an initial $(x_1,y_1)$ position. Following the acquisition of the images at this position, the stage moves to a new $(x_2,y_2)$ position, in a side-wise manner. Then a new set of images is acquired and also stored. As shown in FIG. 9 at a certain step 1, the image segments denoted "1" are captured and stored. In step 2, the segments "2" are stored. In step 3, the segments "3" are stored. The complete image is "composed" in the computer memory as the successive image segments are acquired.

The host computer system that is controlling the above configuration, is driven by software system that controls all mechanical components of the system through suitable device drivers. The software also comprises properly designed image composition algorithms that compose the digitized image in the computer memory and supply the composed image for processing to further algorithms. Through image decomposition, synthesis and image processing specific features particular to the specific sample are detected.

In all automated sample analysis embodiments of the invention, if the generation of the first signal is measured first, indicating cell identity, the one or more smears will be observed using an automated optical microscope to delineate coordinates of a desired number of fetal cells. Only those smears found to contain fetal cells need be treated to generate the second signal, indicating the presence of the particular genetic characteristic being tested for. The automated image analysis algorithms will search for the presence of the second signal at predetermined coordinates of fetal cells and also at predetermined coordinates of control maternal cells. This process could be reversed, whereby the genetic abnormality signal is observed first, and then the cell emitting that signal could be observed to determine whether it is a fetal cell. It is even possible to observe both signals simultaneously, searching only for the simultaneous presence of two signals at a single set of coordinates or even a single signal which results from the interaction of two components (e.g. a quenching of a first signal by a partner 'signal', the first signal being for the cell type and the partner 'signal' being for the genetic abnormality).

The requirements and constraints on the generation of the first and second signals are relatively simple. The materials and techniques used to generate the first signal should not interfere adversely with the materials and techniques used to generate the second signal (to an extent which compromises unacceptably the diagnosis), and visa versa. Nor should they damage or alter the cell characteristics sought to be measured to an extent that compromises unacceptably the diagnosis. Finally, any other desirable or required treatment of the cells should also not interfere with the materials or techniques used to generate the first and second signals to an extent that compromises unacceptably the diagnosis. Within those limits, any suitable generators of the first and second signals may be used.

This exemplary embodiment of the invention may be characterized thus: (i) rather than attempting to enrich (or to further enrich if already partially enriched) the concentration of fetal cells within the maternal blood, fetal cells within the unenriched maternal blood sample are identified for further processing; and (ii) a suitable single cell detection method, such as in situ PCR and/or PCR in situ hybridization is performed to determine the presence of a genetic characteristic being tested for, in some instances only on smears or coordinates of smears that have already been stained and processed, and within which fetal cells have been detected.

Although in an important embodiment, the maternal blood used contains a naturally present concentration of fetal cells, the invention is meant to embrace also maternal blood which has been partially enriched for fetal cells. According to the prior art, the goal was to obtain as much enrichment as possible, to achieve concentrations of fetal cells greater than one fetal cell per 1000 maternal cells. It in particular was the goal to completely isolate fetal cells from maternal cells. According to the invention, cell samples are used where the rare cell is present at no greater than one in every 10,000 cells (i.e. no greater than 0.01%). Thus, simple procedures may be employed to partially enrich the maternal blood sample for fetal cells, such as using simple fractionation procedures (e.g. centrifugation or density gradients) and the like. The procedure falls within the scope of the invention when the sample of cells containing the rare cell is used where the rare cell is present at no greater a concentration than 0.01%. As mentioned above, the invention also in very important embodiments is used where the concentration of the rare cell is 0.001%, 0.0001%, 0.00001%, 0.000001%, and even 0.0000001%. The typical concentration of fetal cells in maternal blood is between one fetal cell in $10^5$ maternal cells to one fetal cell in $10^9$ maternal cells. Thus, the invention is useful over the full-range of concentrations of fetal cells in maternal blood as typically occurs naturally.

In one specific embodiment of the invention, when the rare cell type is present in the sample, the method of the invention detects the rare cell type at a frequency of no less than 80%. In other embodiments, the detection frequencies are no less than 85%, 90%, 95% and 99%.

In addition to the detection of genetic abnormalities in a developing fetus, the above-described method is applicable to any situation where rare event detection is necessary. In particular, the invention can be applied in any situation where a signal from a rare cell is to be detected where the rare cell is present at a concentration no greater than one rare cell for every 10,000 other cells. The invention is particularly applicable to those circumstances where the rare cell can be distinguished phenotypically from the other cells whereby the rare cell first is identified using a first signal, and then the genetic characteristics of the cell identified are determined using a second signal.

Any chromosomal abnormality or Mendelian trait could be diagnosed using the present rare cell technology. The only prerequisite is knowledge of the underlying molecular defect. Use of single fluorophores for the tagging of an individual allele creates an upper limit as to the number of mutations that can be tested simultaneously, however use of combinatorial chemistry increases enormously the number of allele specific mutations that can be tagged and detected simultaneously. Chromosomal abnormalities that fall within the scope of the invention include but are not limited to Trisomy 21, 18, 13 and sex chromosome aberrations such as XXX, XXY, XYY. With the use of combinatorial chemistry, the methods of the invention can be used to diagnose a multitude of translocations observed in genetic disorders and cancer. Mendelian disorders that fall within the scope of the invention include but are not limited to cystic fibrosis, hemochromatosis, hyperlipidemias, Marfan syndrome and other heritable disorders of connective tissue, hemoglobinopathies, Tay-Sachs syndrome or any other genetic disorder for which the mutation is known. The use of combinatorial chemistry dyes allows for the simultaneous tagging and detection of multiple alleles thus making it possible to establish the inheritance of predisposition of common disorders, e.g. asthma and/or the presence of several molecular markers specific for cancers, e.g., prostate, breast, colon, lung, leukemias, lymphomas, etc.

One particularly important use of the invention is in the field of cancer. Cancer cells of particular types often can be recognized morphologically against the background of non-cancer cells. The morphology of cancer cells therefore can be used as the first signal. Heat shock proteins also are markers expressed in most malignant cancers. Labeled antibodies, such as fluorescently-tagged antibodies, specific for heat shock proteins can be used to generate the first signal. Likewise, there are antigens that are specific for particular cancers or for particular tissues, such as Prostate Specific Antigen, and antibodies specific for cancer or tissue antigens, such as Prostate Specific Antigen can be used to generate a first signal for such cancer cells.

Once a cancer cell has been identified by the first signal, a second signal can be generated for providing more information about the cancer. For example, the lifetime risk of breast cancer approaches 80-90% in women with a germ line mutation in either BRCA1 or BRCA2. A variety of mutations in these genes are known and have been reported.

Prostrate cancer is somewhat unique in its presentation to the pathologist of a bewildering array of histologies difficult to assign to diagnostic criteria. It is important to analyze and record the genetic alterations found in prostate cancer, with the objective of correlation to the pathology and natural history of the disease. Such genetic alterations include known alterations in P53, ras, Rb, cyclin-dependent kinases, oncogenes and tumor suppressors. T-cell receptor gene rearrangements are known in large granular lymphocyte proliferations. T-cell receptor delta gene rearrangements are known in acute lymphoblastic leukemia and non-Hodgkin's lymphoma.

Thus, rare cancer cells in a background of other cells can be identified and characterized according to the invention. The characterization may include a confirmation of a diagnosis of the presence of the cancer cell, a determination of the type of cancer, a determination of cancer risk by determining the presence of a marker of a genetic change which relates to cancer risk, etc. Some of the following markers can be used either as the first or the second signals depending on the purpose to which the invention is directed, as will be recognized by those of ordinary skill in the art. The markers include:

Human tumor specific antibody GM4. It preferentially reacts with melanomas and neuroblastomas.

Bone morphogenic proteins (BMPs). Bone metastasis is a common event in prostate cancer and some of the BMPs are expressed in prostate cancer cells.

Growth regulatory genes. Alterations in the structure and expression of growth regulatory genes can lead to the initiation of malignant transformation and tumor progression.

Protein tyrosine kinases. Such kinases are over-expressed in esophageal cancer and play an important role in regulation of proliferation.

Telomerase (hTRT). Elevated expression of hTRT occurs in some cancer tissues.

p53, c-erbB-2 and p21ras. These genes are over expressed in ovarian neoplasms. Development of ovarian carcinoma is the end result of action of several cancer causing genes.

BCL-2 family of proto-oncogenes. These genes are critical regulators of apoptosis whose expression frequently becomes altered in human cancers (including some of the most common types of leukemias and lymphomas).

eKi-ras and c-myc. Mutation of these genes is implicated in tumor initiation and progression in rectal cancer.

APC, p53 and DCC. These are implicated in colorectal tumor carcinogenesis. Treatment strategies need to be coordinated with knowledge of the behavior of the tumor based on its genetic fingerprint.

Markers of genetic changes enable assessment of cancer risk. They provide information on exposure to carcinogenic agents. They can detect early changes caused by exposure to carcinogens and identify individuals with a particularly high risk of cancer development. Such markers include LOH on chromosome 9 in bladder cancer, and chromosome 1p deletions and chromosome 7, 17 and 8 gains/losses detected in colorectal tumorigenesis.

Development of lung cancer requires multiple genetic changes. Activation of oncogenes includes K-ras and myc.

Inactivation of tumor suppressor genes includes Rb, p53 and CDKN2. Identification of specific genes undergoing alteration is useful for the early detection of cells destined to become malignant and permits identification of potential targets for drugs and gene-based therapy.

Mutations in genes that lie in the retinoblastoma pathway are implicated in the pathogenesis of many tumor types. Two critical components involved in tumor progression are p16/CDKN2A and CDK4. Alterations in the former is well documented in multiple cancers including melanoma. Alterations in the latter are rarer.

Mutations in one of four mismatch repair genes (hMSH2, hMLH1, HPMS1 and hPMS2) account for 70% of HNPCC.

Chromosome 11p15.5 is an important tumor suppressor gene region showing LOH in Wilms tumor, rhabdomyosarcoma, adrenocortical carcinoma and lung, ovarian and breast cancer.

Identification of numerically infrequent leukemic cells via unique genomic fusion sequences include MLL-AF4 and PML/RAR (in acute promyelocytic leukemia).

T-cell receptor gene rearrangements are known in large granular lymphocyte proliferations.

T-cell receptor delta gene rearrangements are known in acute lymphoblastic leukemias and non-Hodgkin's lymphoma.

FAP is caused by mutations in the APC gene resulting in multiple adenomas of the colorectal mucosa.

The invention is described in connection with observing "monolayers" of cells. Monolayer has a specific meaning as used herein. It does not require confluence and can involve single cell suspensions. It means simply that the cells are arranged whereby they are not stacked on top of one another, although all of the cells can be separated from one another. Thus, monolayers can be smears of single cell suspensions or can be a thin layer of tissue. Any solid or exfoliative cytology technique can be employed.

The invention also has been described in connection with identifying a pair of signals, one which identifies a target rare cell such as a fetal cell and another which is useful in evaluating the state of the cell such as a fetal cell having a genetic defect. It should be understood that according to certain embodiments, only a single signal need be detected. For example, where a fetal cell carries a Y chromosome and the diagnosis is for an abnormality on the Y chromosome, then the signal which identifies the genetic abnormality can be the same as that which identifies the fetal cell. As another example, a single signal can be employed in circumstances where the observed trait is a recessive trait. A pair of signals also can be used to detect the presence of two alleles or the existence of a condition which is diagnosed by the presence of two or more mutations in different genes. In these circumstances the pair of signals (or even several signals) can identify both the phenotype and the cell having that phenotype. Such embodiments will be apparent to those of ordinary skill in the art.

6. EXEMPLARY EMBODIMENTS

6.1. Smear Preparation

Smears were prepared from 10 µl aliquots of whole blood on glass microscope slides. Smears were prepared from both cord blood and maternal circulating blood and allowed to air dry.

6.1.1. Cell Fixation.

Fixation of smears prior to cell permeabilization for in situ PCR or PCR in situ hybridization was under one of three conditions. (i) Smears were fixed in ice-cold methanol for 10 minutes-16 hours. (ii) Smears were fixed in ice-cold 10% buffered formalin for 10 minutes-16 hours. (iii) Smears were fixed in 2% paraformaldehyde for 10 minutes-16 hours. Following fixation, smears were washed three times in phosphate buffered saline, at room temperature, for 10 minutes. Smears were then air-dried.

6.1.2. Cell Staining

Polychrome Staining:

The smears were covered with Wright's stain and incubated for one to two minutes at room temperature. Distilled water (2.5 ml) was then added to dilute the stain and incubation at room temperature continued for 3-6 minutes. The stain was then washed off rapidly with running water and a 1:10 dilution of Giemsa stain added to the slide. Incubation was at room temperature for 5 minutes and the stain was then washed off rapidly with running water. The smears were then air-dried.

Antibody Staining:

The smears were covered with anti-embryonal hemoglobin (hemoglobin .epsilon.-chain) monoclonal antibody and incubated at room temperature for one to three hours. The slides were then washed twice in phosphate buffered saline, at room temperature, for 5 minutes. Secondary antibody (anti-mouse antibody conjugated to phycoerythrin) was then added and the slide incubated at 37° C. for 30 minutes. The slides were then washed twice in phosphate buffered saline, at room temperature, for 5 minutes and air-dried.

Fetal Hemoglobin Staining:

Smears were fixed in 80% ethanol for 5 to 10 minutes, then rinsed with tap water and air dried. Acid citrate-phosphate buffer (37.7 ml 0.1M citric acid, 12.3 ml 0.2M $Na_2HPO_4$, pH 3.3) was pre-warmed in a coplin jar in a 37° C. water bath. The fixed smears were then added to the coplin jar and incubated at 37° C. for 5 minutes. The smears were then rinsed with tap water and stained with 0.1% hematoxylin for one minute. The smears were then rinsed with tap water and stained with 0.1% eosin for one minute. The smears then underwent a final rinse in tap water and were air-dried.

Cell Permeabilization:

Cell permeabilization was attained by incubation in either proteinase K (1-5 mg/ml in phosphate buffered saline) or pepsin (2-5 mg/ml in 0.01M hydrochloric acid). Incubation was at room temperature for 1-30 minutes. Following permeabilization, smears were washed in phosphate buffered saline, at room temperature, for 5 minutes, then in 100% ethanol, at room temperature, for one minute. Smears were then air-dried.

PCR In Situ Hybridization:

For PCR in situ hybridization, smears were overlaid with 50 µl amplification solution. Amplification solution comprised 10 mM Tris-HCl, pH 8.3, 90 mM potassium chloride, 1-5 mM magnesium chloride, 200 µM dATP, 200 µM dCTP, 200 µM dGTP, 200 µM dTTP, 1 µM forward primer, 1 µM reverse primer and 5-10 units thermostable DNA polymerase in aqueous sealing reagent. A glass coverslip was then lowered onto the amplification solution and the slide transferred to a thermal cycler. Following an initial denaturation step at 94° C. for 4 minutes, the slide was then subjected to 25-35 cycles of amplification, where each cycle consisted of denaturation at 94° C. for one minute, annealing at 55° C. for one minute and extension at 72° C. for one minute. The coverslip was then removed by incubation of the slide in phosphate buffered saline for 10 minutes at room temperature, and the slide air-dried. Fluorescein labeled oligonucleotide probe in hybridization buffer (600 mM sodium chloride, 60 mM sodium citrate, 5% dextran sulfate, 50% formamide) was then added and the slide covered with a glass cover slip, and incubated at 94° C. for 10 minutes then at 37° C. for one hour. The coverslip was then removed by incubation of the slide in phosphate buffered saline for 10 minutes at room temperature and the slide then washed twice for 5 minutes in phosphate buffered saline at room temperature. The smear was then covered with protein block solution (1% bovine serum, 2.5% goat serum, 0.2% Tween-20) and incubated at room temperature for 10 minutes. The solution was then removed and the slide washed three times in phosphate buffered saline for 5 minutes at room temperature. The smear was then covered with mouse anti-fluorescein monoclonal antibody and incubated at room temperature for 20 minutes. The solution was then removed and the slide washed three times in phosphate buffered saline for 5 minutes at room temperature. The smear was then covered with biotinylated goat anti-mouse $F(ab)_2$ and incubated at room temperature for 20 minutes. The solution was hen removed and the slide washed three times in phosphate buffered saline for 5 minutes at room temperature. The smear was then covered with alkaline phosphatase conjugated streptavidin and incubated at room temperature for 20 minutes. The solution was then removed and the slide washed twice in phosphate buffered saline for 5 minutes at room temperature. Alkaline phosphatase substrate solution (50 mg/ml BCIP, 75 mg/ml NBT) was then added to the smear and the slide incubated at 37° C. for 10 minutes-two hours. The slide was then washed twice in distilled water at room temperature for 5 minutes and air-dried.

In Situ PCR:

For in situ PCR, smears were overlaid with 50 l amplification solution. Amplification solution comprised 10 mM Tris-HCl, pH 8.3. 90 mM potassium chloride, 15 mM magnesium chloride, 200 μM dATP, 200 μM dCTP, 200 .mu.M dGTP, 0.5 μM [R110]dUTP, 1 μM forward primer, 1 μM reverse primer and 5-10 units thermostable DNA polymerase in aqueous sealing reagent. A glass coverslip was then lowered onto the amplification solution and the slide transferred to a thermal cycler. Following an initial denaturation step at 94° C. for 4 minutes, the slide was then subjected to 25-35 cycles of amplification, where each cycle consisted of denaturation at 94°. C. for one minute, annealing at 55° C. for one minute and extension at 72° C. for one minute. The coverslip was then removed by incubation of the slide in phosphate buffered saline for 10 minutes at room temperature and the slide air-dried.

6.2. Automated Smear Analysis

Automated smear analysis has been briefly summarized, above. The apparatus and method used in the exemplary embodiment is now described.

6.2.1. Apparatus

Figure 2:
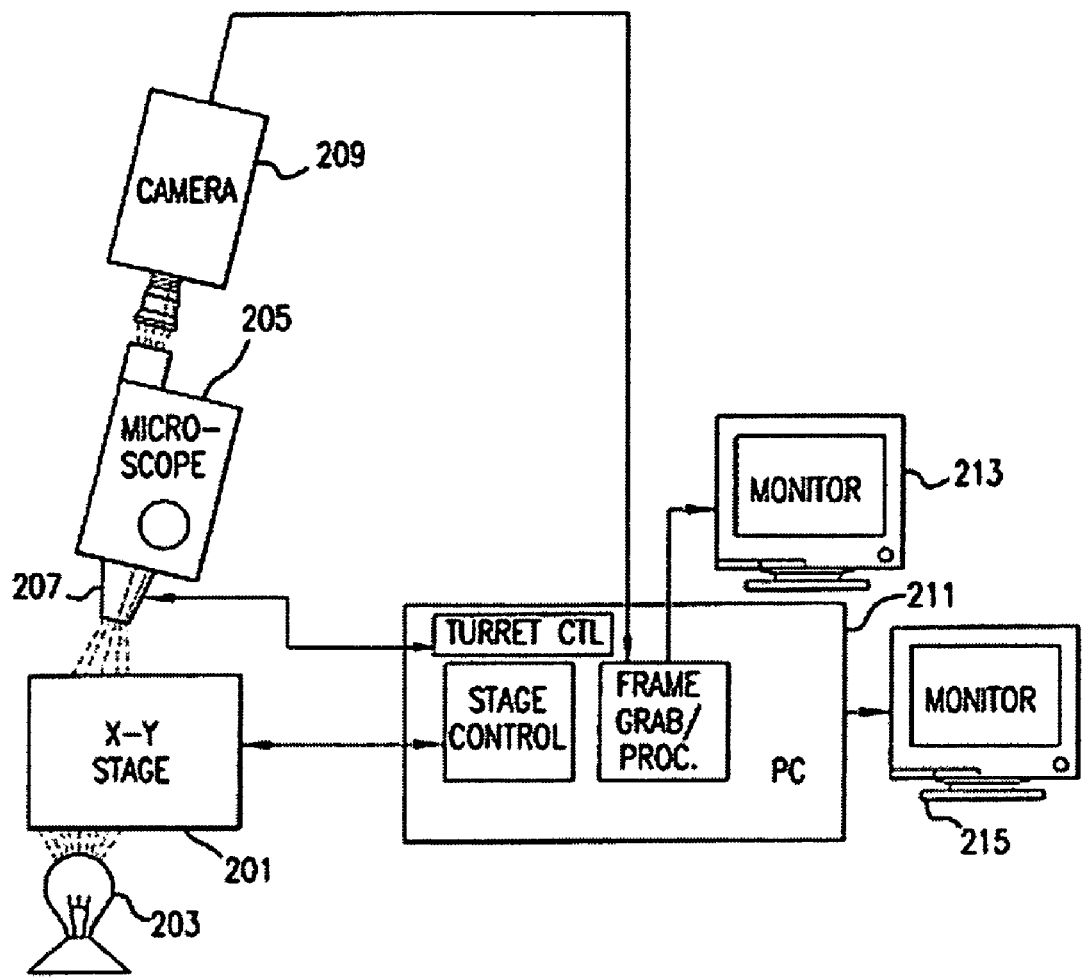
FIG. 2 is a block diagram of an analysis system used in one embodiment of one aspect of the invention.

The block diagram of FIG. 2 shows the basic elements of a system suitable for embodying this aspect of the invention. The basic elements of the system include an X-Y stage 201, a mercury light source 203, a fluorescence microscope 205 equipped with a motorized objective lens turret (nosepiece) 207, a color CCD camera 209, a personal computer (PC) system 211, and one or two monitors 213, 215.

The individual elements of the system can be custom built or purchased off-the-shelf as standard components. Each element will now be described in somewhat greater detail.

The X-Y stage 201 can be any motorized positional stage suitable for use with the selected microscope 205. Preferably, the X-Y stage 201 can be a motorized stage that can be connected to a personal computer and electronically controlled using specifically compiled software commands. When using such an electronically controlled X-Y stage 201, a stage controller circuit card plugged into an expansion bus of the PC 211 connects the stage 201 to the PC 211. The stage 201 should also be capable of being driven manually. Electronically controlled stages such as described here are produced by microscope manufacturers, for example including Olympus (Tokyo, Japan), as well as other manufacturers, such as LUDL (NY, USA).

The microscope 205 can be any fluorescence microscope equipped with a reflected light fluorescence illuminator 203 and a motorized objective lens turret 207 with a 20× and an oil immersion 60× or 63× objective lens, providing a maximum magnification of 600×. The motorized nosepiece 207 is preferably connected to the PC 211 and electronically switched between successive magnifications using specifically compiled software commands. When using such an electronically controlled motorized nosepiece 207, a nosepiece controller circuit card plugged into an expansion bus of the PC 211 connects the stage 201 to the PC 211. The microscope 205 and stage 201 are set up to include a mercury light source 203, capable of providing consistent and substantially even illumination of the complete optical field.

The microscope 205 produces an image viewed by the camera 209. The camera 209 can be any color 3-chip CCD camera or other camera connected to provide an electronic output and providing high sensitivity and resolution. The output of the camera 209 is fed to a frame grabber and image processor circuit board installed in the PC 211. A camera found to be suitable is the SONY 930 (SONY, Japan).

Various frame grabber systems can be used in connection with the present invention. The frame grabber can be, for example a combination of the MATROX IM-CLD (color image capture module) and the MATROX IM-640 (image processing module) set of boards, available from MATROX (Montreal, CANADA). The MATROX IM-640 module features on-board hardware supported image processing capabilities. These capabilities compliment the capabilities of the MATROX IMAGING LIBRARY (MIL) software package. Thus, it provides extremely fast execution of the MIL based software algorithms. The MATROX boards support display to a dedicated SVGA monitor. The dedicated monitor is provided in addition to the monitor usually used with the PC system 211. Any monitor SVGA monitor suitable for use with the MATROX image processing boards can be used. One dedicated monitor usable in connection with the invention is a ViewSonic 4E (Walnut Creek, Calif.) SVGA monitor.

In order to have sufficient processing and storage capabilities available, the PC 211 can be any INTEL PENTIUM-based PC having at least 32 MB RAM and at least 2 GB of hard disk drive storage space. The PC 211 preferably further includes a monitor. Other than the specific features described herein, the PC 211 is conventional, and can include keyboard, printer or other desired peripheral devices not shown.

6.2.2. Method

The PC 211 executes a smear analysis software program compiled in MICROSOFT C++ using the MATROX IMAGING LIBRARY (MIL). MIL is a software library of functions, including those which control the operation of the frame grabber 211 and which process images captured by the frame grabber 211 for subsequent storage in PC 211 as disk files. MIL comprises a number of specialized image processing routines particularly suitable for performing such image processing tasks as filtering, object selection and various measurement functions. The smear analysis software program runs as a WINDOWS 95 application. The program prompts and measurement results are shown on the computer monitor 213, while the images acquired through the imaging hardware 211 are displayed on the dedicated imaging monitor 215.

In order to process microscopic images using the smear analysis program, the system is first calibrated. Calibration compensates for day to day variation in performance as well as variations from one microscope, camera, etc., to another. During this phase a calibration image is viewed and the following calibration parameters are set:

the color response of the system;

the dimensions or bounds of the area on a on a slide containing a smear to be scanned for fetal cells;

the actual dimensions of the optical field when using magnifications 20.times. and 60× (or 63×); and the minimum and maximum fetal nuclear area when using magnifications 20.times. and 60× (or 63×).

6.2.3. Detection of the First (Identification) Signal

The fetal cell detection algorithm operates in two stages. The first is a pre-scan stage I, illustrated in the flow chart of FIG. 3, where possible fetal cell positions are identified using a low magnification and high speed. The 20× objective is selected and the search of fetal cells can start:

The program moves the automated stage (FIG. 2, 201) to a preset starting point, for example one of the corners of a slide containing a smear (Step 301).

The x-y position of the stage at the preset starting point is recorded (Step 303) optical field.

The optical field is acquired (Step 305) using the CCD camera 209 and transferred to the PC 211 as an RGB (Red/Green/Blue) image.

The RGB image is transformed (Step 307) to the ILLS (Hue/Luminance/Saturation) representation.

The Hue component is binary quantized (Step 309) as a black and white image so that pixels with Hue values ranging between 190 and 255 are set to 0 (black) representing interesting areas (blobs), while every other pixel value is set to 255 (white, background). The blobs represent possible fetal cell nuclear areas.

The area of each blob in the binary quantized image is measured. If, at 20.times. magnification, it is outside a range of about 20 to 200 pixels in size, the blob's pixels are set to value 255 (background); they are excluded from further processing (Steps 311, 313, 315 and 317).

Then the coordinates of each blob's center of gravity (CG) are calculated (Step 319), using a custom MATROX function. The center of gravity of a blob is that point at which a cut-out from a thin, uniform density sheet of material of the blob shape would balance. These coordinates are stored in a database along with the z-y position of the current optical field, so the blob can be located again at the next processing stage using higher magnification.

Additional optical fields are processed similarly, recording the x-y position of each succeeding optical field, until the complete slide are is covered (Steps 321 and 323).

Stage II, illustrated in the flow chart of FIGS. 4A and 4B, includes the final fetal cell recognition process:

63.times. magnification is selected (Step 401).

The program moves the automated stage (FIG. 2, 201) so that the coordinates of the first position of a CG found earlier, which is possible fetal cell nuclear area, is at the center of the optical field (Step 403).

The optical field is acquired using the CCD camera (FIG. 2, 209) and transferred to the computer as an RGB image (Step 405).

The RGB image is transformed to the HLS model (Step 407).

The program then generates a Luminance histogram (Step 409) by counting the number of pixels whose Luminance value equals each possible value of Luminance. The counts are stored as an array of length 256 containing the count of pixels having a grey-level value corresponding to each index into the array.

The program next analyzes the Luminance distribution curve (Step 411), as represented by the values stored in the array, and locates the last peak. It has been found that this peak includes pixel values that represent plasma area in the image. The function that analyzes the Luminance distribution curve: calculates a 9-point moving average to smooth the curve; calculates the tangents of lines defined by points 10 grey-level values distant; calculates the slopes of these lines in degrees; finds the successive points where the curve has zero slope and sets these points (grey-levels) as −1 if they represent a minimum (valley in the curve) or 1 if they represent a maximum (peak in the curve); then finds the locations of peaks or valleys in the curve by finding the position of a 1 or a −1 in the array of grey-level values.

The program then sets as a cut-off value the grey-level value of pixels lying in the valley of the Luminance distribution which occurs before the last peak of the distribution (Step 413).

Using this cut-off value, the program then produces (Step 415) a second binary quantized image. This is a black-and-white image in which pixels corresponding to pixels in the Luminance image having grey-level values lower than the cut off point are set to 255 (white) and pixels corresponding to pixels in the Luminance image having grey-level values higher than the cut off point are set to 0 (black). The white blobs of this image are treated as cells while the black areas are treated as non-cellular area.

A closing filter is applied (Step 417) to the second binary quantized image; in this way holes, i.e., black dots within white regions, are closed.

The program now measures the area of the cells. If the area of any of the cells is less than 200 pixels then these cells are excluded, i.e. the pixels consisting these cells are set to pixel value 255 (black) (Step 419).

A hole fill function, found in the MIL, is applied to the remaining blobs (Step 412). The resulting binary quantized image, after processing, is a mask whose white regions denote only cells.

Red blood cells are now distinguished from white blood cells based on the Saturation component of the HLS image. The mask is used to limit processing to only the cell areas.

The program now counts the number of pixels whose Saturation value is each possible value of Saturation. The counts are stored as an array of length 256 containing the count of pixels having a grey-level value corresponding to each index into the array (Step 423).

The program now analyzes (Step 425) the Saturation distribution curve, as represented by the values stored in the array, and locates the first peak. This peak includes pixel values that represent areas contained in white blood cells.

The grey-level value that coincides with the first minimum (valley) after the peak is set as a cut-off point (Step 427).

Using this cut-off value the program produces (Step 429) a third binary quantized image. Pixels corresponding to pixels in the Saturation image having grey-level values higher than the cut-off point are set to 255 (white). They constitute red blood cell areas. Pixels corresponding to pixels in the Saturation image having grey-level values lower than the cutoff point are set to 0 (black). The white blobs of this third binary quantized image are seeds for areas that belong to red blood cells.

A closing filter is applied (Step 431) to the third binary quantized image; in this way holes, i.e., black dots within white regions, are closed.

A hole fill function, found in the MIL, is applied (Step 433) to the remaining blobs. The resulting binary quantized image, after processing, is a new mask that contains only white blood cells.

An erase border blob function of MIL is now applied (Step 435) to the remaining blobs, removing those which include pixels coincident with a border of the image area. Such blobs cannot be included in further processing as it is not known how much of the cell is missing when it is coincident with a border to the image area.

An erosion filter is applied 6 times to this mask; thus any connected blobs (white blood cell seeds) are disconnected (Step 437).

A "thick" filter is applied 14 times (Step 439). The "thick" filter is equivalent to a dilation filter. That is, it increases the size of a blob by successively adding a row of pixels at the periphery of the blob. If a growing blob meets an adjacent blob growing next to it, the thick filter does not connect the two growing blobs. Thus adjacent blobs can be separated.

The first binary quantized mask (containing all the cells) and the third binary quantized mask (containing the separated seeds of white blood cells) are combined with a RECONSTRUCT_FROM_SEED MIL operator. A fourth mask thus constructed contains blobs (cells) copied from the first mask that are allowed by the third mask and therefore represent white blood cells (Step 441).

The blobs in the fourth mask are measured for their area and compactness: Area (A) is the number of pixels in a blob; Compactness is derived from the perimeter (p) and area (A) of a blob, it is equal to: $p^2/4(A)$. The more convoluted the shape, the bigger the value. A circle has the minimum compactness value (1.0). Perimeter is the total length of edges in a blob, with an allowance made for the staircase effect which is produced when diagonal edges are digitized (inside corners are counted as 1.414, rather than 2.0). Blobs are retained in the fourth mask only if their area is between 1000 and 8000 pixels and they have a compactness less than 3, thus allowing for cells with relatively rough outline. Blobs that touch the border of the image are excluded from further processing (Step 443).

The fourth mask is applied to the Hue component in the following manner (Steps 445, 447, 449 and 451):

Pixels from the Hue component are copied to a new image retaining their Hue value, provided that their coordinates coincide with white (255) pixels in the "mask"; all other pixels in the new image are set to 0 (black) (Step 445).

The pixel values in each of the contiguous non-0 pixel areas, i.e., those blobs corresponding to images of red cells, are checked for values between 190 and 255. The number of such pixels in each blob is counted (Step 447).

If there are more than 200 such pixels, the blob represents a nucleated red blood cell. The coordinates of the center of gravity of each such cell are stored. The mask is binary quantized so that all pixels having non-0 values are set to 255 (white); and the mask is stored as a separate Tagged Image File Format (TIFF) file (Step 449).

The program moves to the next stored coordinates for a possible fetal cell which do not coincide with any of the coordinates stored during the previous step. The entire process is repeated until a preset number of nucleated red blood cells have been identified. The results, including the nucleated red blood cell coordinates and the names of the respective mask files, along with various characteristic codes for the blood slide are stored in a result text file. The nucleated red blood cells whose coordinates are stored are the fetal cells sought (Step 451).

After fetal cells are identified, the second signal is generated, for example by in situ CR or PCR in situ hybridization or FISH, as described above.

6.2.4. Detection of the Second Signal

A smear including in situ PCR or PCR in situ hybridization treated cells is positioned on the stage (FIG. 2, 201). If necessary calibration steps are taken, as before. Calibration permits the software to compensate for day to day variation in performance as well as variations from one microscope, camera, etc. to another. Detection of the second signal then proceeds, as shown in the flow chart of FIG. 5, as follows:

Magnification objective 60× (63×) is chosen (Step 501).

The x-y stage is moved to the first fetal cell position according to data from the result file compiled from detection of the first signal, as described above (Step 503).

The optical field is acquired using the CCD camera (FIG. 2, 209) and transferred to the computer (FIG. 2, 211) as an RGB image (Step 505).

The RGB image is transformed to the HLS model (Step 507).

The TIFF file containing the black and white mask is loaded as a separate image (Step 509).

The pixels of the Hue component not corresponding to white areas in the mask arc set to 0 (black) (Step 511).

The remaining areas, which represent fetal cells, are searched for pixel values corresponding to a signal produced following PCR. For example, the signal may be a color which arises due to the presence of alkaline phosphatase, i.e., red. The non black areas of the Hue component are searched for pixel values ranging from 0 to 30 (Step 513).

The stage is moved to the next non-processed fetal cell and the above process is repeated (Step 515).

6.3. Variations

A number of variations on the above-described system and method are also contemplated and are encompassed by the present invention. Some of these are now described. This description will also suggest others to those skilled in the art.

Each unenriched blood sample may be used to prepare smears on each of a plurality of individual microscope slides. When prepared in this way, each slide can undergo detection of the first signal. However, only those slides which the first signal is detected need be further processed to generate the second signal, and subsequently are analyzed to detect the second signal. Processing in this way permits the use of conventional sample and slide-handling equipment.

In a variation illustrated schematically in FIG. 6, the unenriched blood sample 601 is used to prepare a single, long smear on a flexible substrate 603. The substrate 603 can have a length 10 or more times its width. For example, a strip of cellulose acetate film base with sprocket holes on either side could be used as the substrate. The strip carrying the smear undergoes the processing steps described above in a continuous processing system, as shown in FIG. 6. After locations of fetal cells are determined by detection of the first signal, segments of the smear including those locations are cut out of the continuous strip for generation and detection of the second signal.

In an alternative processing method using a single, long smear on a flexible substrate, the strip is divided into a plurality of individual segments similar to microscope slides, before generating and detecting the first signal. Processing proceeds as for individual microscope slides.

The above variations, and similar variations, are advantageous in that the entire smear need not be processed for generation and detection of the second signal. Only those slides or segments in which the first signal is detected need undergo the further processing to generate and detect the second signal.

In one aspect of the invention, a device is provided for dispensing reagents only to those portions of the smear where a rare cell is detected. Referring to FIG. 7, an apparatus of the invention is shown including a reagent dispenser system. The reagent dispenser system can be located for dispensing reagents to precise locations on the stage. This is particularly suited for dispensing reagents only of the coordinates identified by a first signal, such as the coordinates of a rare cell (e.g., a fetal cell and a maternal blood smear). The system includes a reagent dispenser 701 which is a housing for one or more micropipettes located within the housing. The reagent dispenser is attached in this embodiment to the microscope and is positioned relative to the stage in fixed relation to the microscope. The narrow tip of the reagent dispenser 701 is adjacent the stage 201. The opposite end of the reagent dispenser 701 has communicating therewith feedline 703 which is a tube or a housing carrying a plurality of tubes for delivering reagents to the reagent dispenser 701. The feedline 703 is attached remote from the reagent dispenser 701 to a first reagent container 705 and a second reagent container 707. In the embodiment shown, the feedline 703 is a housing through which passes feedline 703' communicating with reagent container 705 and feedline 703' communicating with reagent container 707. A pump 709 is attached to feedline 703" for pumping reagent from the reagent container 707 to the reagent dispenser 701, and out the narrow tip of the reagent dispenser 701 onto the stage at a desired location. Another pump 709' is attached to feedline 703' for delivering reagents from reagent container 705 to the reagent dispenser 701. The pumps are electronically controlled by PC211 using specifically compiled software commands indicated by "reagent control". The reagents can be any one of the reagents described above in connection with generating a signal.

In the embodiment shown, the reagent dispenser is attached to the microscope. The reagent dispenser need not be attached to the microscope and, instead, can be otherwise attached to any frame relative to the X-Y stage. The stage is shown as moving with respect to the reagent dispenser for locating the narrow tip of the reagent dispenser at a precise location with respect to a slide on the stage. The slide on the stage can be moved to a different location, and the reagent dispenser can be itself moveably controlled to locate it relative to a set of coordinates in the slide. What is important is that, in an automated fashion, the coordinates of a detected rare cell can be positioned with respect to the dispensing end of the reagent dispenser, whereby materials may be delivered to a discrete location at the coordinates of the rare cell. If the reagent dispenser is controlled by a motor and moveable with respect to a stage or a slide upon a stage, then the reagent dispenser can be provided with a sensor for locating its position with respect to the slide or stage. Thus, the slide on a stage can be processed in series, with the microscope first locating the coordinates on the slide of the rare cell. The slide then is next moved to a second processing area where the reagent dispenser is positioned at the previously-identified coordinates in the slide and reagents are delivered to generate the second signal. Optionally the slide could be moved to a third station, such as a thermocycling station and then back to the microscope field for viewing.

It should be evident that different treatments of the smear are possible when it is desired to identify a different cell type or to diagnose a different cellular characteristic. The biochemistry, morphological parameters and colors described above may each be varied in known ways to meet other diagnostic needs.

Computer and image processing technologies are constantly changing. Newer technologies which meet the needs of the above-described methods and apparatus, while not specifically described here, are clearly contemplated as within the invention. For example, certain conventional pixel and image file formats are mentioned above, but others may also be used. Image files may be compressed using JPEG or GIF techniques now known in the art or other techniques yet to be developed. Processing may be performed in an RGB color description space instead of the HLS space currently used. Other color spaces may also be used, as desired by the skilled artisan, particularly when detection of a sought-after characteristic is enhanced thereby.

While the embodiments of the invention have been described in connection with unenriched samples of maternal blood, aspects of the invention may be practiced on conventionally enriched or partially enriched maternal blood samples, as well. The use of a computer-controlled microscopic vision system to identify and to diagnose fetal cells within the sample is applicable to samples covering a full range of fetal cell concentrations. As has been discussed above, the use of such a system is particularly advantageous when used in connection with unenriched maternal blood samples.

The present invention has now been described in connection with a number of particular embodiments thereof. Additional variations should now be evident to those skilled in the art, and are contemplated as falling within the scope of the invention, which is limited only by the claims appended hereto and equivalents thereof.

The invention claimed is:

1. An automated method implemented on a computerized automated microscopy system operatively configured to search a microscope slide, said method comprising the steps of:
   receiving a microscope slide with a cell sample, comprising at least one said rare cell, affixed as a monolayer, said cell sample having been treated with an identification label selective to physical characteristics, of a rare cell, and a diagnostic label indicative of an abnormality;
   automatically detecting, by said computerized automated microscopy system, the position of said rare cell based upon detection of said identification label position in said monolayer;
   automatically detecting by said computerized automated microscopy system whether a signal indicative of said diagnostic label is proximate with said detected identification label position; and
   automatically providing a putative diagnosis of said abnormality based on detection of said diagnostic label being proximate with the position of said at least one identification label.

2. The method of claim 1, wherein the rare cell is present at no greater than 0.001% of cells in said cell sample.

3. The method of claim 2, wherein the rare cell is present at no greater than 0.0001% of cells in said cell sample.

4. The method of claim 1, wherein the rare cell is present at no greater than 0.00001% of cells in said cell sample.

5. The method of claim 1, wherein the computerized automated microscopy system used has two or more objectives.

6. The method, in accordance with claim 1, wherein the step of receiving a microscope slide with a cell sample is performed by a sample storage and loading and unloading module and a sample transporting mechanism that moves the sample under a microscope objective lens to and from an automated stage.

7. A method for using a computerized automated microscopy system operatively configured to automatically search a microscope slide to detect signals from said slide, and to process said signals, said method comprising the steps of:
receiving a microscope slide with a cell sample, comprising at least one said rare cell, affixed as a monolayer, such that the monolayer comprises no greater than one rare cell in 10,000 cells, wherein said cell sample is treated with an identification label of said rare cell to identify said rare cell with a signal detectable by said automated microscopy system, and treated with a diagnostic label indicating the presence of a particular abnormality, said diagnostic label producing a signal which is detectable by said automated microscopy system;
detecting by said automated microscopy system a signal indicative of said identification label associated with said rare cell and from said signal detected automatically determining the position of said rare cell on said slide;
detecting by said automated microscopy system a signal indicative of said diagnostic label proximate with said determined position of said rare cell(s);
automatically providing a putative diagnosis based on detection of said diagnostic label being proximate with the detected position of said at least one rare cell.

8. The method of claim 7, wherein the rare is present at no greater than 0.001% of cells in said cell sample.

9. The method of claim 8, wherein the rare is present at no greater than 0.0001% of cells in said cell sample.

10. The method of claim 9, the rare is present at no greater than 0.00001% of cells in said cell sample.

11. The method of claim 7, wherein the selective identification signal is processed to represent morphological measurements of the rare cell.

12. The method of claim 7, further comprising the steps of:
treating said rare cell(s) labeled with said identification label with another identification label to enhance optical distinction of rare cell(s) from other cell(s).

13. The method of claim 7, wherein the computerized automated microscopy system used in the method has two or more objectives.

14. The method, in accordance with claim 7, wherein the step of receiving a microscope slide with a cell sample is performed by a sample storage and loading and unloading module and a sample transporting mechanism that moves the sample under a microscope objective lens to and from an automated stage.

15. A method, implemented on a computerized microscope, comprising:
receiving a biological sample on a substrate as a monolayer of a sample including the rare cell;
searching said substrate for a first signal indicative of location of said rare cell;
detecting a second signal indicative of an abnormality at the proximate location of said first signal; and
providing a diagnosis of said abnormality of said rare cell based on said second signal.

16. The method, in accordance with claim 15, wherein the step of receiving a biological sample is performed by a sample storage and loading and unloading module and a sample transporting mechanism that moves the sample under a microscope objective lens to and from an automated stage.

17. A method for detecting a clinical abnormality associated with a rare cell using a computerized microscope, comprising:
forming on a substrate a monolayer of a sample including the rare cell;
searching the substrate for a first signal indicative of location of said rare cell;
positioning the microscope relative to the first signal to detect a second signal indicative of abnormality of said rare cell; and
providing a diagnosis of said abnormality of the rare cell based on detection of said second signal.

18. A method of obtaining from a sample of cells, a signal having diagnostic significance relative to a rare cell in the sample of cells, comprising the steps of:
receiving a monolayer of the sample of cells fixed on a substrate, wherein one or more rare cell(s) of interest is present in the monolayer sample at no greater than one in every 10,000 cells;
contacting the rare cell(s) of interest with an agent to generate a diagnostic signal associated with one or more components of in each of said rare cell of interest;
automatically determining the position of one or more said rare cell(s) of interest on said slide using a computerized microscopic vision system;
automatically determining whether a diagnostic signal is associated with the determined position of each of said rare cells of interest using said computerized microscopic vision system.

19. The method of claim 18, wherein the rare cell is present at no greater than 0.001% of cells in said cell sample.

20. The method of claim 18, wherein the rare cell is present at no greater than 0.0001% of cells in said cell sample.

21. The method of claim 18, the rare cell is present at no greater than 0.00001% of cells in said cell sample.

22. The method of claim 18, further comprising the step of:
contacting said sample with an agent to generate a locating signal with respect to said rare cell of interest.

23. The method of claim 22, further comprising: determining the location of said rare cell(s) by way of said locating signal.

24. The method of claim 22, further comprising of: further processing the locating signal to represent morphological measurements of the rare cell(s).

25. The method of claim 18 wherein the sample of cells is derived from maternal blood and the rare cell(s) is a fetal cell.

26. The method, in accordance with claim 18, wherein the step of receiving a monolayer of the sample of cells fixed on a substrate is performed by a sample storage and loading and unloading module and a sample transporting mechanism that moves the sample under a microscope objective lens to and from an automated stage.

27. A method, implemented in a computerized microscopic vision system, of obtaining from a sample of maternal blood containing a naturally present concentration of fetal cells, a signal having diagnostic significance relative to the fetal cells, the method comprising:
receiving a smear of a sample of maternal blood on a substrate, said sample having been contacted with an identification label identifying, by a first signal, fetal cells in said maternal blood and a diagnostic agent to generate a second signal; said second signal having diagnostic significance;
observing the smear using a computerized microscopic vision system operatively configured to read said substrate and to obtain and record location of said first signal indicative of the presence of said fetal cell;
observing the fetal cell using the computerized microscopic vision system to obtain the second signal; and counting occurrences of the second signal in a plurality of fetal cells eliciting said first signal, comparing count of said occurrences with predefined value to provide a diagnosis.

28. The method of claim 27, wherein the first signal is further processed to represent morphological measurements of the fetal cells.

29. The method of claim 27, wherein the first signal and the second signal do not mask one another when both are present.

30. The method of claim 27, further comprising the step of: calibrating a coordinate system to said substrate so that coordinates of said fetal cell(s) identified at one point in time can be returned to at a later point of time.

31. The method of claim 27, wherein the computerized microscopic vision system has two or more objectives.

32. The method, in accordance with claim 27, wherein the step of receiving a smear of the sample of maternal blood on a substrate is performed by a sample storage and loading and unloading module and a sample transporting mechanism that moves the sample under a microscope objective lens to and from an automated stage.

* * * * *